US009574232B2

(12) United States Patent
Han et al.

(10) Patent No.: US 9,574,232 B2
(45) Date of Patent: Feb. 21, 2017

(54) DEVICES AND METHODS FOR CONTROLLING REVERSIBLE CHEMICAL REACTIONS AT SOLID-LIQUID INTERFACES BY RAPID PRECONCENTRATION AND PHASE REPLACEMENT

(71) Applicant: The Board of Trustees of the Leland Stanford Junior University, Palo Alto, CA (US)

(72) Inventors: Crystal Han, Stanford, CA (US); Juan G. Santiago, Stanford, CA (US); Viktor Shkolnikov, Chatsworth, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 171 days.

(21) Appl. No.: 14/630,623

(22) Filed: Feb. 24, 2015

(65) Prior Publication Data
US 2016/0177382 A1 Jun. 23, 2016

Related U.S. Application Data

(60) Provisional application No. 61/944,308, filed on Feb. 25, 2014.

(51) Int. Cl.
| | |
|---|---|
| *G01N 27/447* | (2006.01) |
| *G01N 27/00* | (2006.01) |
| *C12M 1/34* | (2006.01) |
| *C12Q 1/68* | (2006.01) |
| *G01N 33/53* | (2006.01) |
| *C40B 30/04* | (2006.01) |
| *C07H 21/02* | (2006.01) |
| *C07H 21/04* | (2006.01) |
| *G01N 27/27* | (2006.01) |
| *C07K 1/22* | (2006.01) |
| *G01N 30/60* | (2006.01) |

(52) U.S. Cl.
CPC .............. *C12Q 1/6837* (2013.01); *C07K 1/22* (2013.01); *C12Q 1/6832* (2013.01); *G01N 27/27* (2013.01); *G01N 27/44704* (2013.01); *G01N 27/44791* (2013.01); *G01N 27/447* (2013.01); *G01N 27/44795* (2013.01); *G01N 30/60* (2013.01)

(58) Field of Classification Search
CPC ......... C12Q 1/68; C12M 1/34; G01N 27/447; C07H 21/02; C40B 30/04
USPC .... 204/549, 645; 435/6.1, 7.1, 287.2; 506/9; 536/23.1, 24.3
See application file for complete search history.

(56) References Cited

U.S. PATENT DOCUMENTS

| | | | |
|---|---|---|---|
| 8,021,531 B2* | 9/2011 | Park | B01F 5/0646 204/451 |
| 8,394,251 B2 | 3/2013 | Santiago et al. | |
| 8,524,061 B2 | 9/2013 | Utz et al. | |
| 8,614,059 B2 | 12/2013 | Young et al. | |
| 8,846,314 B2 | 9/2014 | Chambers et al. | |
| 8,865,401 B2 | 10/2014 | Young et al. | |
| 2004/0118688 A1* | 6/2004 | Dumas | G01N 27/44704 204/548 |
| 2009/0269767 A1* | 10/2009 | Soderlund | B01L 3/50273 435/6.11 |
| 2010/0084271 A1* | 4/2010 | Santiago | C12Q 1/686 204/549 |
| 2010/0224494 A1* | 9/2010 | Chambers | C12N 15/101 204/549 |
| 2011/0036718 A1 | 2/2011 | Jung et al. | |
| 2012/0175258 A1 | 7/2012 | Mariella et al. | |
| 2013/0175173 A1* | 7/2013 | Ivory | G01N 27/44717 204/547 |

OTHER PUBLICATIONS

Shkolnikov et al Coupling Isotachophoresis with Affinity Chromatography for Rapid and Selective Purification with High Column Utilization, Part 2: Experimental Study, 2014, Ananl. Chem., 86, 6229-6236.*
Smejkal et al, Microfluidic isotachophoresis: A review, 2013, Electrophoresis, 34, 1493-1509.*
Garcia-Schwarz et al, Integration of On-Chip Isotachophoresis and Functionalized Hydrogels for Enhanced-Sensitivity Nucleic Acid Detection, 2012, Anal. Chem., 84, 6366-6369.*
Rogacs et al, Purification of nucleic acids using isotachophoresis, 2014, Journal of Chromatography A, 1335, 105-120.*
Bahga et al. (2013) Integration of rapid DNA hybridization and capillary zone electrophoresis using bidirectional isotachophoresis. Analyst 138(1):87-90.
Bercovici (2012) Rapid hybridization of nucleic acids using isotachophoresis. Proc. Natl. Acad. Sci. U.S.A. 109(28):11127-11132.
Persat et al. (2011) MicroRNA profiling by simultaneous selective isotachophoresis and hybridization with molecular beacons. Anal. Chem. 83(6):2310-2316.
Garcia-Schwarz et al. (2012) On-chip isotachophoresis for separation of ions and purification of nucleic acids. J. Vis. Exp. (61):e3890.
Garcia-Schwarz et al. (2012) Rapid high-specificity microRNA detection using a two-stage isotachophoresis assay. Angew Chem Int Ed Engl. Oct. 25, 2013;52(44):11534-11537.

(Continued)

*Primary Examiner* — Narayan Bhat
(74) *Attorney, Agent, or Firm* — Jenny Buchbinder

(57) ABSTRACT

Devices and methods for controlling reversible chemical reactions at solid-liquid interfaces are disclosed. In particular, the invention relates to a method of increasing reaction rates by concentrating a target molecule in a liquid phase in the region of a reactant or ligand immobilized on a solid followed by removal of the liquid phase and replacement with an immiscible phase, such as an immiscible gas or liquid to impede the reverse reaction. Devices for performing this method to increase the rates and degree of completion of kinetically limited ligand binding or nucleic acid hybridization reactions in affinity chromatography and microarray applications are also disclosed.

12 Claims, 21 Drawing Sheets

(56) References Cited

OTHER PUBLICATIONS

Eid et al. (2013) Isotachophoresis with ionic spacer and two-stage separation for high sensitivity DNA hybridization assay. Analyst. 138(11):3117-3120.
Goet et al. (2009) Micro contactor based on isotachophoretic sample transport. Lab Chip 9(24):3586-3593.

* cited by examiner

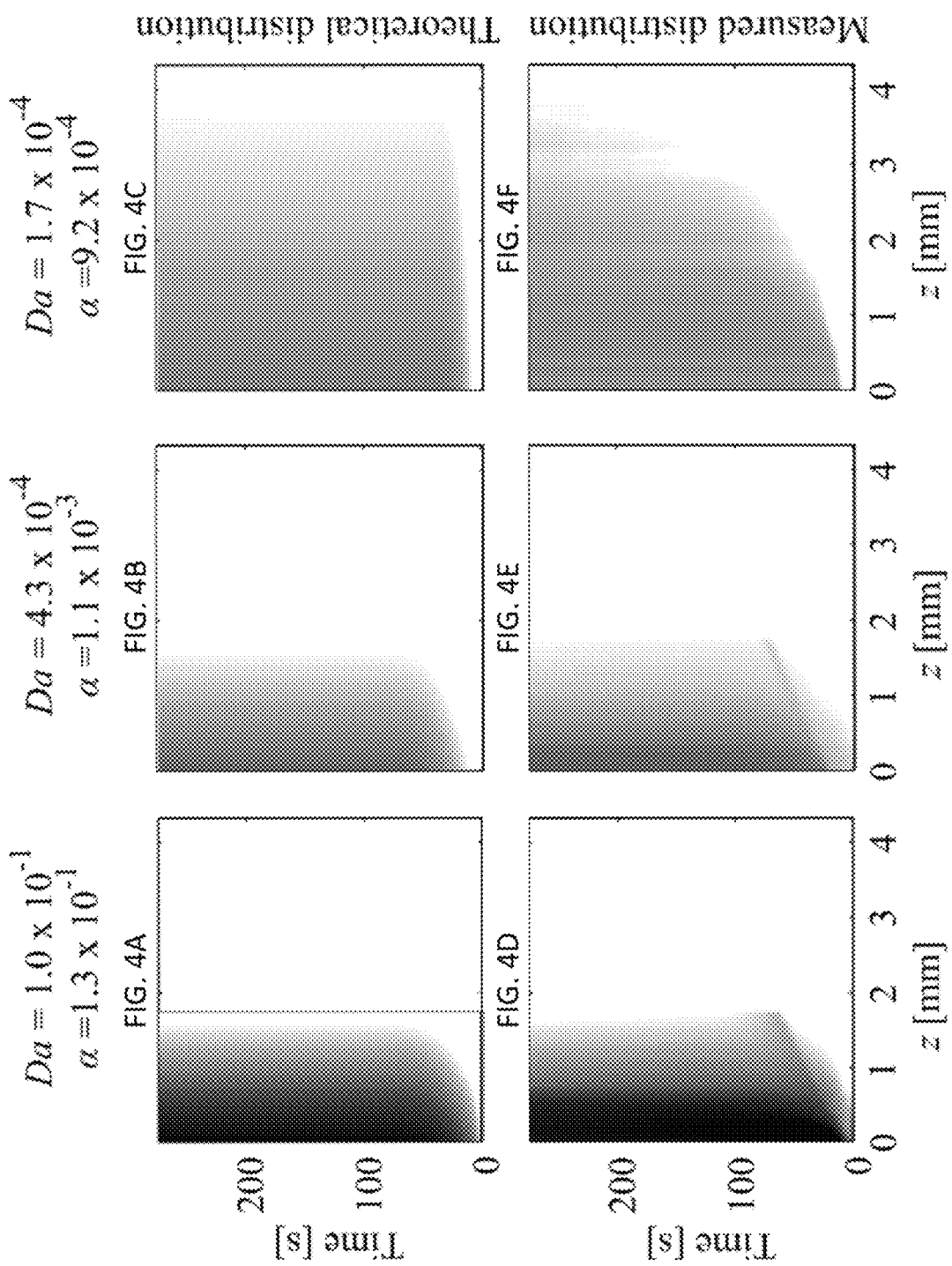

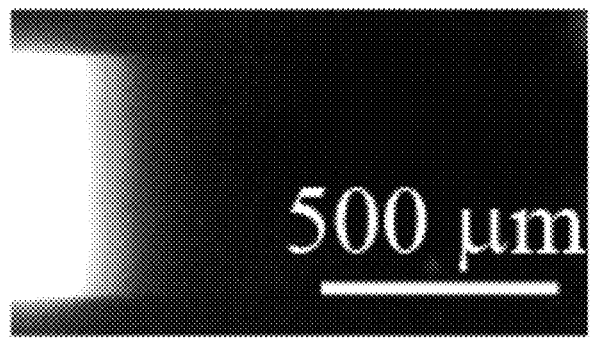
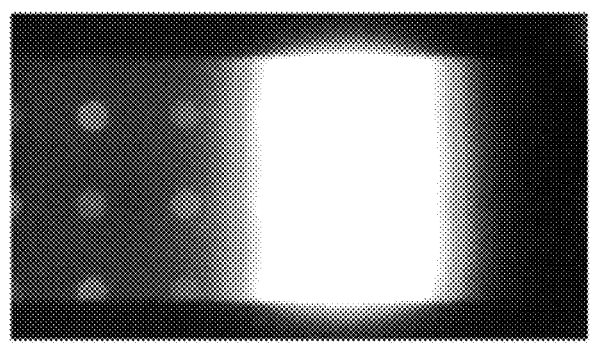
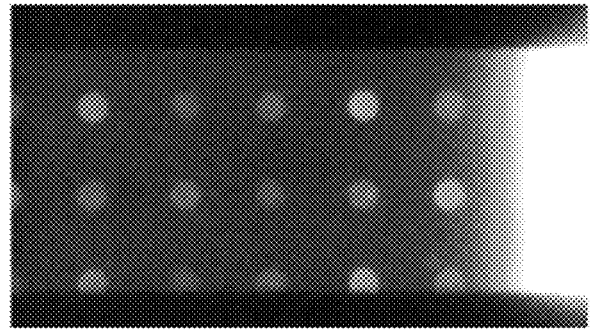
FIG. 7B

DEVICES AND METHODS FOR CONTROLLING REVERSIBLE CHEMICAL REACTIONS AT SOLID-LIQUID INTERFACES BY RAPID PRECONCENTRATION AND PHASE REPLACEMENT

CROSS-REFERENCE TO RELATED APPLICATION

This application claims benefit under 35 U.S.C. §119(e) of provisional application 61/944,308, filed Feb. 25, 2014, which is hereby incorporated by reference in its entirety.

STATEMENT REGARDING FEDERALLY SPONSORED RESEARCH OR DEVELOPMENT

This invention was made with Government support under contract HR0011-12-C-0080 awarded by the Defense Advanced Research Project Agency. The Government has certain rights in this invention.

TECHNICAL FIELD

The present invention pertains generally to devices and methods for controlling reversible chemical reactions at solid-liquid interfaces using preconcentration of reactants and phase replacement.

BACKGROUND

ITP is an electrokinetic technique used to preconcentrate and separate ionic analytes (Everaerts et al., Isotachophoresis: Theory, Instrumentation, and Applications, Elsevier, Amsterdam, New York, 1976; Bocek, Analytical Isotachophoresis, VCH, Cambridge, 1987; Garcia-Schwarz et al. (2012) JoVE e3890). The ITP method involves introduction of a sample comprising an analyte of interest between a zone containing a "fast" migrating leading electrolyte (LE) and a zone containing a "slow" migrating trailing electrolyte (TE). The LE and TE are chosen such that the mobility of the analyte of interest is higher in the TE zone than that of the TE co-ion and lower in the LE zone than that of the LE co-ion. Analytes can be co-focused by this method into a relatively narrow peak at the interface of the LE and TE electrolytes (Garcia-Schwarz et al., supra; Khurana et al. (2008) Anal. Chem. 80:6300; Garcia-Schwarz et al. (2011) J. Fluid Mech. 679:455).

Affinity chromatography (AC) is a chromatographic technique that leverages a specific binding agent, the affinity ligand, for purification, separation, and/or analysis of sample components. The affinity ligand (probe) is used to selectively yet reversibly capture the sample component of interest (target). Numerous samples and sample components are analyzed or purified using AC, including enzymes, lectins, other proteins, and nucleic acids (Hage, Handbook of Affinity Chromatography, CRC Press, Boca Raton, 2006; Hage (1999) Clin. Chem. 45:593; Mallik et al. (2006) J. Sep. Sci. 29:1686; Pfaunmiller et al. (2013) Anal. Bioanal. Chem. 405:2133). For many samples, including important biological samples (e.g., blood, cell lysate), the component of interest is present in very low concentrations, while background, potentially fouling species are present in relatively high concentrations. This necessitates that a substantial volume of sample be processed through the affinity substrate. Additionally, low target concentrations imply low target-probe binding rates (Levenspiel, Chemical Reaction Engineering John Wiley & Sons, New York, 1999). These factors increase the time of the affinity assay, can lead to poor substrate utilization, and/or poor purification yield, limiting applications of the method. The aforementioned limitations of AC can be addressed by increasing the forward binding rate of reactions (Levenspiel, supra), but this binding rate is often difficult to improve upon (Hage, supra).

ITP has been used in conjunction with affinity assays in several applications. For example, Abelev et al. used ITP with counterflow to transport sample compounds onto regions of immobilized proteins on cellulose acetate and nitrocellulose membrane (Abelev et al. (1988) Bull. Exp. Biol. Med. 106:1600; Abelev et al. (1989) Mol. Immunol. 26:49; Abelev et al. (1989) Mol. Immunol. 26:41; Abelev et al. (1988) Bull. Exp. Biol. Med. 105:748; Schranz et al. (1991) Electrophoresis 12:414; Abelev and Karamova, in Serological Cancer Markers, Springer, 1992, p. 453; Abelev et al. (1994) Mol. Biol. (Mosk) 28:768). Abelev et al. used the binding to detect the presence of and analyze properties of antibodies, proteins, lectins, and nucleic acids. However, in their work, ITP was used only as a pump-free, reproducible transport mechanism, and not to substantially preconcentrate the analytes or speed up reactions (Abelev et al. (1994), supra). More recently, Garcia-Schwartz et al. presented an approach combining ITP and an affinity reaction to detect micro-RNA (Garcia-Schwarz et al. (2012) Anal. Chem. 84:6366; Garcia-Schwarz et al. (2013) Angew. Chem. 125:11748). They used ITP to accelerate hybridization between a target and a mobile fluorescent DNA probe in a microchannel. This ITP zone was then transported into a channel section containing cross-linked polyacrylamide gel functionalized with DNA complementary to the fluorescent DNA probe. This method was used to remove signal background (a negative enrichment strategy) and enhance sequence specific quantitation (Garcia-Schwarz et al. (2012), supra; Garcia-Schwarz et al. (2013), supra).

Microarray technology enables the investigation of on the order of 10,000 sequences in parallel (Lander (1999) Nat. Genet. 21:3-4). This high-throughput capability and sensitivity has been leveraged in a wide range of applications, including gene expression analysis (Ross et al. (2000) Nat. Genet. 24:227-235; Adomas et al. (2008) Tree Physiol. 28:885-897; Schena et al. (1995) Science 270:467-470), diagnosis of diseases (Marx (2000) Science 289:1670-1672; Wallace (1997) Mol. Med. Today 3:384-389; Shen et al. (2009) Clin. Chem. 55:659-669), single nucleotide polymorphism (SNP) (Hacia et al. (1999) Nat. Genet. 22:164-167; Chen et al. (2003) Pharmacogenomics J. 3:77-96), and aptamer-based analysis of protein biomarkers (Gold et al. (2010) PLoS One 5:e15004; Kraemer et al. (2011) PLoS One 6:e26332). DNA arrays use hybridization between a mixture of targets suspended in a bulk sample solution and probes immobilized on a solid substrate. Despite its proven success, application of DNA arrays to rapid screening of samples remains a challenge (Teles et al. (2008) Talanta 77:606-623). The hybridization alone in conventional microarray experiments typically requires overnight (15-24 hours) incubation to yield measurable signal from target molecules at a wide range of target concentrations (Hegde et al. (2000) J. Biotechniques 29:548-550, 552-554, 556 passim; Cheung et al. (1999) Nat. Genet. 21(1 Suppl):15-19). This constraint has limited the application of microarrays in point-of-care applications where short turnaround time is desirable. Reduction in hybridization time is also favorable because extended incubation times are associated with solution-dependent cleavage of the linkage chemistry between the probe and the solid support, negatively affecting the reproducibility and sensitivity (Situma et al. (2006) Biomol. Eng. 23:213-231).

There are two main challenges in speeding up hybridization processes: overcoming the slow diffusion-limited target transport and the slow reaction rates associated with low target concentrations (Pappaert et al. (2003) Chem. Eng. Sci. 58:4921-4930). The vast majority of work toward speeding up DNA array hybridization has involved addressing the first of these limitations with active pumping and/or mixing of liquid solution containing the molecular target (Wang et al. (2011) Anal. Chim. Acta 687:12-27). Successful microarray hybridization speed-up has been demonstrated using syringe pump-driven mixing (McQuain et al. (2004) Anal. Biochem. 325:215-226), microfluidic integrated peristaltic pump mixing (Liu et al. (2006) Angew Chem. Int. Ed. Engl. 45(22): 3618-3623), mixing using 7 mm scale magnetic stir bars (Yuen et al. (2003) Lab Chip 3:46-50), pumping and mixing discrete sample plugs through serpentine microchannels (Wei et al. (2005) Nucleic Acids Res. 33:e78), acoustic microstreaming (Liu et al. (2003) Anal. Chem. 75:1911-1917), pumping with displacement micropumps, centrifugal liquid pumping (Wang et al. (2010) Anal. Biochem. 400: 282-288; Peytavi et al. (2005) Clin. Chem. 51:1836-1844; Chen et al. (2008) Lab Chip 8:826-829), pneumatically driven mixing (Wang et al. (2011) J. Talanta 84:565-571; Adey et al. (2002) Anal. Chem. 74:6413-6417), and electrokinetic sample dispensing and washing (Erickson et al. (2004) Anal Chem. 76(24):7269-7277).

The aforementioned methods of active pumping and vigorous mixing help hybridization rate as they create conditions where fresh sample at its original concentration is driven toward ligands on the surface, avoiding diffusion limited regime. However, these approaches do not address the challenge of kinetically limited reactions associated with low target concentrations. Kinetically limited reaction between suspended DNA with surface-bound cDNA can take hours to reach equilibrium due to the inherent dynamics of bulk-to-surface reactions (Gao et al. (2006) Nucleic Acids Res. 34:3370-3377; Okahata et al. (1998) Anal. Chem. 70:1288-1296). Kinetically limited hybridization is therefore not addressed by pumping or mixing, but rather by preconcentration of target species or methods of increasing kinetic parameters themselves (e.g., varying temperature). An example of preconcentration-driven reaction rate enhancement is the work of Edman et al. (Nucleic Acids Res. (1997) 25:4907-4914), who demonstrated 30-fold increased hybridization rate by electrophoretically accumulating DNA species at the capture probes immobilized on the surface of positively biased microelectrodes. This method received much attention for a brief time, but was largely abandoned by the field, possibly due to its strict microfabrication requirements, and the strong sensitivity of hybridization reactions to the effects of electrochemical reactions (which can damage DNA, dramatically change local pH, and/or generate bubbles due to water hydrolysis).

Thus, there remains a need for methods of increasing the rates of kinetically limited ligand binding or nucleic acid hybridization reactions, particularly in affinity chromatography and microarray applications.

SUMMARY

The present invention relates to devices and methods for controlling reversible chemical reactions at solid-liquid interfaces by concentrating a reactant in a liquid phase in the vicinity of another reactant on the surface of a solid to increase the rate of reaction and subsequently replacing the liquid phase with an immiscible phase that impedes the reverse reaction. Exemplary devices for performing the methods described herein to increase the rate and degree of completion of a kinetically limited ligand binding or nucleic acid hybridization reaction in affinity chromatography and microarray applications are described in Examples 1 and 2.

In one aspect, the invention includes a method of increasing the rate and degree of completion of a reaction between a first reactant in a liquid phase and a second reactant on the surface of a solid, the method comprising: a) contacting the solid with the liquid phase; b) concentrating the first reactant in the liquid phase near the second reactant on the surface of the solid; c) reacting the first reactant in the liquid phase with the second reactant on the surface of the solid; and d) removing the liquid phase, whereby the reverse reaction is impeded. The liquid phase can be removed by displacing the liquid phase with an immiscible phase, such as a gas or immiscible liquid.

In one embodiment, the invention includes a method of increasing the rate and degree of completion of a reaction between a first reactant in a liquid phase and a second reactant on the surface of a solid, the method comprising: a) contacting the solid with the liquid phase; b) performing isotachophoresis (ITP) on the liquid phase using a trailing electrolyte (TE) and a leading electrolyte (LE), such that the first reactant in the liquid phase is concentrated at a LE-TE interface near the second reactant on the surface of the solid; c) reacting the first reactant in the liquid phase with the second reactant on the surface of the solid; and d) removing the liquid phase, whereby the reverse reaction is impeded.

In certain embodiments, the reaction comprises binding of the first reactant to the second reactant, for example, binding of an analyte to an affinity ligand or hybridization of a nucleic acid with a nucleic acid probe.

In certain embodiments, the first reactant or the second reactant is selected from the group consisting of a nucleic acid, a modified nucleic acid, an oligonucleotide, a ligand, a receptor, a hormone, an antibody, an antigen, an enzyme, a substrate, an inhibitor, an activator, a cofactor, a drug, a lipid, a carbohydrate, a glycoprotein, a lectin, an extracellular matrix component, a small organic molecule, and an inorganic molecule. In one embodiment, the second reactant is an affinity ligand immobilized on the surface of the solid. In another embodiment, the second reactant is a nucleic acid probe immobilized on the surface of the solid.

In certain embodiments, the solid comprises a methacrylate-based polymer, polyether sulfone, agarose, cellulose, a polysaccharide, polytetrafluoroethylene, polysulfone, polyester, polyvinylidene fluoride, polypropylene, poly (tetrafluoroethylene-co-perfluoro(alkyl vinyl ether)), polycarbonate, polyethylene, glass, polyacrylate, polyacrylamide, poly (azolactone), polystyrene, polydivinylbenzene, polylactide, ceramic, nylon or metal. The solid may comprise an affinity chromatography matrix or a porous polymer monolith (PPM). In one embodiment, the solid comprises a PPM comprising poly(glycidyl methacrylate-co-ethylene dimethacrylate) (GMA-EDMA).

In certain embodiments, ITP is performed with the LE and TE in solution at a pH between 4 and 10. In one embodiment, the pH is between about 8.0 and about 8.3. In one embodiment, the initial TE ion concentration is about 0.5 to about 0.8 of the LE ion concentration. Electrolytes that can be used include, but are not limited to TRIS and HCl as the LE or 6-aminocaproic acid and HCl as the LE, HEPES and TRIS as the TE, HEPES and BIS-TRIS as the TE, HEPES and histidine as the TE, MES and TRIS as the TE, MES and BIS-TRIS as the TE, MES and histadine as the TE, caproic acid and TRIS as the TE, caproic acid and BIS-TRIS as the TE, caproic acid and histadine as the TE, and caproic acid and β-alanine as the TE. For example, ITP can be performed with a solution containing an LE comprising Tris and HCl and a solution containing a TE comprising HEPES and TRIS or BIS-TRIS (see Examples 1 and 2).

In another embodiment, the method further comprises adding an agent for suppressing electroosmotic flow. Agents for suppressing electroosmotic flow include, but are not limited to polylactams, substituted polyacrylamide derivatives, water soluble methylhydroxyethyl derivatives of cellulose, polyvinylalcohol, polyvinylpyrrolidones, and polyethyleneglycols. In one embodiment, the polylactam is polyvinylpyrrolidone.

In another embodiment, the method further comprises adding a detectable label to a reactant. In one embodiment, the detectable label is a fluorophore.

In another aspect, the invention includes a device for performing ITP in combination with affinity chromatography according to the methods described herein. In one embodiment, the device comprises: a) a tube comprising an input end and an output end; b) an affinity region comprising a plurality of affinity ligands immobilized on a solid support, wherein the affinity region is located inside the tube; c) a first reservoir comprising the TE, wherein the first reservoir is connected to the input end of the tube; and d) a second reservoir comprising the LE, wherein the second reservoir is connected to the output end of the tube. The solid support may comprise a conventional affinity chromatography matrix or a PPM. In certain embodiments, the PPM is composed of an acrylate, methacrylate, vinylpyridine, vinylpyrrolidone, vinylbenzene, divinylbenzene, or vinyl acetate-based polymer. In certain embodiments, the solid support comprises pores of at least about 1 micron in diameter. In one embodiment, the solid support comprises pores of about 1 micron to about 2 micron in diameter. In certain embodiments, the tube is a capillary or a chromatography column. In another embodiment, the device is a microfluidic device and the tube is a microfluidic channel within the microfluidic device. Preferably, the affinity region has a hydrodynamic resistance low enough to allow the tube to be filled without the use of a high pressure pump. An exemplary device is described in Example 1.

In one embodiment, the invention includes a method for performing affinity chromatography with such a device, the method comprising: a) filling the second reservoir and the tube with a solution comprising the LE; b) adding a solution comprising a target molecule and the TE to the first reservoir; c) performing isotachophoresis (ITP), such that the target molecule is concentrated at a LE-TE interface in the affinity region; d) capturing the target molecule by binding the target molecule to an affinity ligand in the affinity region; e) removing the solution comprising the LE and the solution comprising the TE; and f) eluting the target molecule. In one embodiment, the method comprises filling the second reservoir with a solution comprising the LE and applying a vacuum to the first reservoir to draw the solution comprising the LE into the tube. In another embodiment, removing the solution comprising the LE and the solution comprising the TE comprises displacing the solution by adding a gas or an immiscible liquid that impedes the reverse reaction.

In another aspect, the invention includes a device for performing ITP in combination with microarray analysis according to the methods described herein. In one embodiment, the device comprises: a) a microarray comprising a plurality of nucleic acid probes immobilized on a solid support; b) a fluidic channel containing the microarray, wherein the fluidic channel comprises an input end and an output end and a constriction located between the input end and the microarray; c) a first reservoir comprising the TE, wherein the first reservoir is connected to the input end of the fluidic channel; and d) a second reservoir comprising the LE, wherein the second reservoir is connected to the output end of the fluidic channel. The fluidic channel may be a capillary or a chromatography column. In one embodiment, the device is a microfluidic device and the fluidic channel is a microfluidic channel within the microfluidic device. In one embodiment, the constriction of the fluidic channel is narrow enough to result in uniform dispersion of the first reactant by diffusion. In one embodiment, the microfluidic channel comprises an elastomer (e.g., polydimethylsiloxane (PDMS)). Example 2 describes an exemplary microfluidic device comprising a microfluidic channel about 500 µm wide, 80 mm long, and 40 µm deep with a 200 µm wide constriction.

In another aspect, the invention includes a method of fabricating a microfluidic device for performing ITP in combination with microarray analysis, the method comprising: a) creating a master mold of the microfluidic device; b) casting an elastomer microfluidic chip from the master mold; c) creating holes at the locations of the first reservoir and the second reservoir; d) immobilizing the plurality of nucleic acid probes on the solid support to form the microarray; and e) pressing the elastomer microfluidic chip onto the solid support comprising the microarray. Methods for fabricating such a device are described in Example 2.

In one embodiment, the invention includes a method of performing microarray analysis with such a device, the method comprising: a) filling the fluidic channel with a solution comprising the LE; b) filling the second reservoir with a gel comprising the LE; c) adding a sample comprising target nucleic acids and the TE to the first reservoir; d) performing isotachophoresis (ITP) until the LE-TE interface reaches the constriction; e) turning off the electric field for a period of time sufficient to allow the nucleic acids to distribute across a cross-section of the fluidic channel by diffusion; f) applying a low electric field, such that target nucleic acids concentrated over the microarray hybridize to the nucleic acid probes of the microarray while unbound nucleic acids continue to migrate downstream of the microarray; and g) detecting hybridization. In one embodiment, the method further comprises labeling the nucleic acids in the sample with a detectable label, for example, with a fluorophore or other label. At least one agent for reducing nucleic acid secondary structure (e.g., detergent or formamide) may be mixed with the sample to improve hybridization.

In certain embodiments, the low electric field is applied at a constant current ranging between about 2 µA to about 16 µA or about 2 µA to about 4 µA, including any level of current within these ranges, such as 2, 3, 4, 5, 6, 7, 8, 9, 10, 11, 12, 13, 14, 15, or 16 µA.

In certain embodiments, when the LE-TE interface reaches the constriction, the electric field is turned off for about 1 to about 5 minutes, including any time within this range such as 1, 2, 3, 4, or 5 minutes to allow diffusion of the nucleic acids. In one embodiment, the electric field is turned off for about 2 minutes to allow diffusion of the nucleic acids. In one embodiment, the constriction is narrow enough to result in uniform dispersion of nucleic acid analytes during diffusion.

In another aspect, the invention provides a kit for increasing the rate and degree of completion of a chemical reaction at a solid-liquid interface according to the methods described herein. The kit may include one or more agents for performing ITP (e.g., electrolytes, buffers, and electrodes) and a solid support comprising at least one immobilized reactant. In one embodiment, the kit further comprises a gas or immiscible liquid to be used for phase replacement. The kit may further provide printed instructions for carrying out ITP in order to enhance the rate of a chemical reaction. In one embodiment, the kit comprises a device for performing ITP in combination with affinity chromatography as described herein. In another embodiment, the kit comprises a device for performing ITP in combination with microarray analysis as described herein. The kit may further comprise reagents and equipment for performing ITP (e.g., electrolytes, buffer, electrodes), affinity chromatography (e.g., affinity chromatography media or PPM, activating agent, eluent), or microarray analysis (e.g., microarray, reagents for detectably labeling nucleic acids). The kit may further comprise information, in electronic or paper form, comprising instructions for performing the methods described herein.

These and other embodiments of the subject invention will readily occur to those of skill in the art in view of the disclosure herein.

BRIEF DESCRIPTION OF THE FIGURES

FIG. 1A shows a schematic illustrating our assay for ITP-aided affinity chromatography in a porous polymer monolith column. We first fill the LE reservoir and affinity column with LE buffer, and mix the sample containing the target into the TE in the TE reservoir (Step 1). We then apply an electric field and the target separates, concentrates (over 100-fold) and focuses into a sharp peak (Step 2). The target then migrates into the affinity region and is captured by the immobilized probe (Step 3). After capture, we remove the LE and TE buffers and elute the bound target with an elution buffer (Step 4). FIG. 1B shows a SEM micrograph of our custom PPM substrate for probe immobilization. The PPM was composed of globules ~1 μM in diameter that formed ~2 μm diameter pores ensuring that the porous affinity region had small hydrodynamic resistance. FIG. 1C shows a spatiotemporal plot of measured target concentration showing dynamics of a typical ITP-AC binding experiment. The concentrated target (visualized with Cy5 fluorescence) entered the porous affinity region on the right and was captured by the immobilized probes. In this experiment $Da=1.0\times10^{-4}$, $\alpha=1.3\times10^{-3}$.

In FIG. 2A, for a particular Da/α and α for which Da≤1, $p_z^*$ is invariant of α. We term the value of α that for a particular Da/α gives Da=1 "critical α". For α greater then a critical α, the scaled capture length increases linearly with α as the affinity region becomes locally saturated. In FIG. 2B, scaled capture time $p_t\ k_1N$ increases exponentially with Da/α Da/α<1. For Da/α>1, scaled capture time increases linearly with Da/α. Interestingly, the scaled capture time is independent of total scaled target amount, Da (i.e., the length scale of capture region is insensitive to capture amount provided ligand is not saturated). In FIG. 2C, n/N increases linearly with α for α less than the critical α (where the affinity region is not saturated). For α larger than the critical α, the affinity region becomes locally saturated and n/N=1.

FIGS. 3A-3C show spatiotemporal plots of n/N for $Da=4.3\times10^{-4}$ and $\alpha=1.1\times10^{-3}$ and β values of $10^{-6}$, $10^{-1}$, and 3, respectively. This set of Da and α is similar to that in the experiment described in FIG. 4E. FIG. 3D shows n/N scaled by Da for values of β between $10^{-6}$ and 1, Da/α between 0.01 and 100, and α between 0.01 and 100. As β increases the reverse reaction (dissociation) becomes more prominent until no effective binding occurs and the target streaks through the affinity region. Capture efficiency n/N always decreases with increasing β, while decreasing values of Da/α and α mitigate this effect. Decreasing Da/α (e.g., by preconcentrating the target with ITP) allows one to achieve larger capture efficiencies for a given dissociation constant. Furthermore, increasing scaled peak concentration α increases the decrease in capture efficiency with increasing β and therefore it is important to not locally overload the affinity region for maximum target capture.

FIGS. 4A-4F show theoretically predicted (FIGS. 4A-4C) and experimentally visualized (FIGS. 4D-4F) spatiotemporal behavior of ITP-AC in the affinity region. The spatiotemporal plots show the logarithm of cross-sectional area averaged fluorescence intensity of the target as a function of axial coordinate z and time. FIGS. 4A-4C show theoretically predicted captured target distribution for $Da=1.0\times10^{-1}$, $\alpha=1.3\times10^{-1}$, $Da=4.3\times10^{-4}$, $\alpha=1.1\times10^{-3}$, and $Da=1.7\times10^{-4}$, $\alpha=9.2\times10^{-4}$ respectively. FIGS. 4D-4F show experimentally observed capture target distribution for the same respective Da and α. For both experimental conditions the theoretically predicted spatiotemporal distribution of target agreed well with that experimentally observed. We attribute the "tails" in FIGS. 4D and 4E to small amounts impurity present with the target that did not get captured by the affinity probes.

FIG. 6A shows the separation observed in the SYBR Green I channel showing the migration of SYBR Green I visualized fish sperm (background) DNA and Cy 5 visualized target from free solution into the porous polymer. Here only SYBR Green I visualized fish sperm DNA can be observed. Fish sperm DNA was not captured by the immobilized probe on the PPM and continued to migrate in ITP. This indicated that there was little non-specific binding of DNA to PPM. FIG. 6B shows the separation observed in the Cy5 channel showing the migration of SYBR Green I visualized fish sperm DNA and Cy 5 visualized target from free solution into the porous polymer. Here only Cy5 visualized target can be observed. Cy5 visualized target was captured by the immobilized probe on the PPM. FIG. 6C shows the separation observed in overlapped SYBR Green I and Cy5 channels clearly showing the separation between rare target DNA from 10,000-fold more abundant contaminating DNA fish sperm DNA.

Figure 7A:
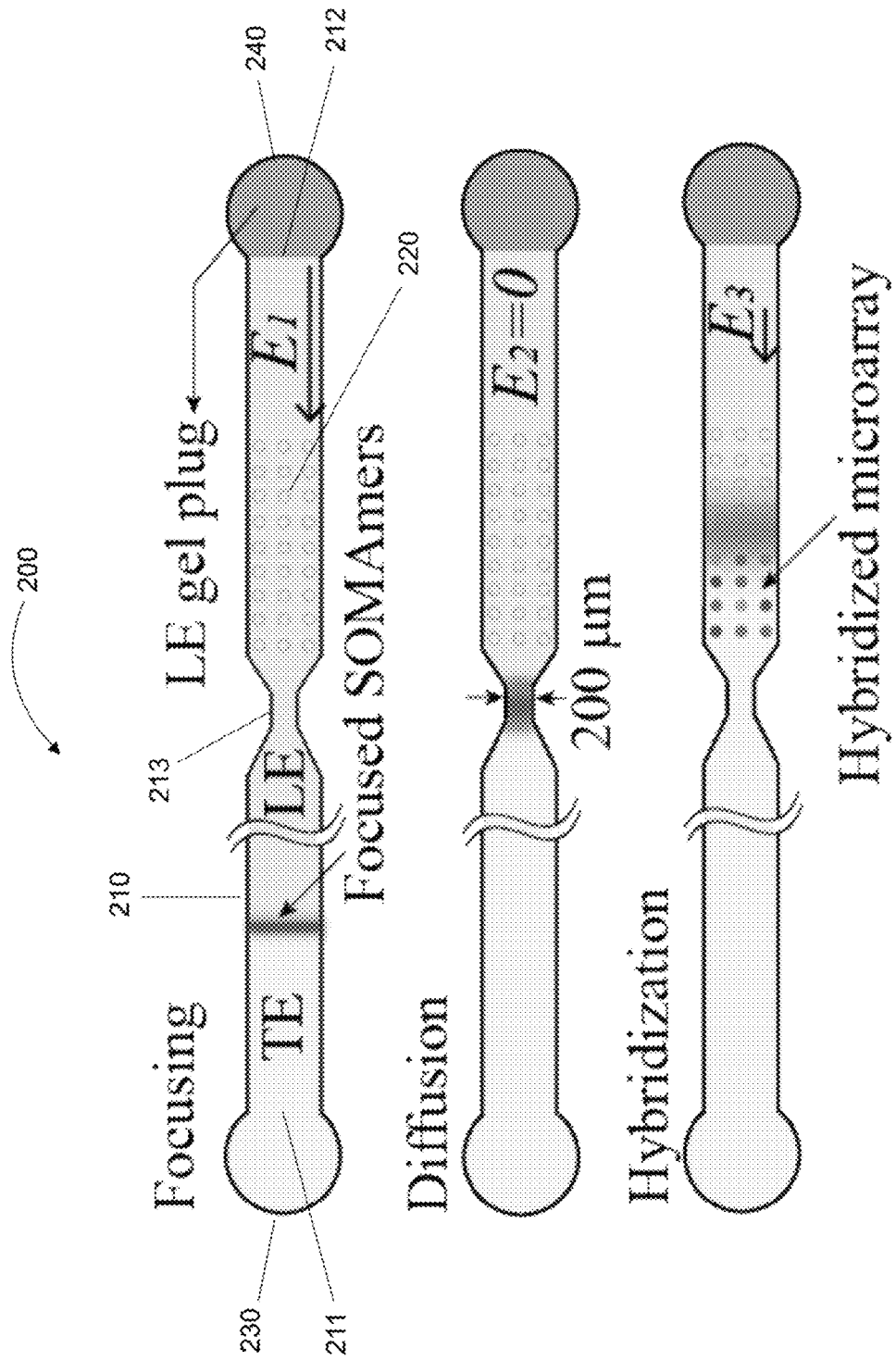

FIGS. 7A and 7B show a schematic of the ITP hybridization assay. FIG. 7A illustrates the three step protocol of ITP hybridization: focusing, diffusion, and hybridization. Target single-stranded (ssDNA) electromigrates and accumulate at the interface of TE and LE under high electric field during the focusing step. As the ITP zone reaches the constriction of the channel, the electric field is turned off, and target DNA is redistributed uniformly across the cross section of the channel by diffusion for 2 minutes. In the hybridization step, low electric field is applied to avoid further instability and focused target sweeps over the immobilized probes, and speeds up the binding reaction. FIG. 7B shows an experimental demonstration of ITP microarray hybridization with images taken at three times. The ITP-focused Cy3 labeled ssDNA targets migrated over the surface immobilized complimentary probes. After the ITP zone swept by, we observed the fluorescence signal increase at the probe sites. The initial concentration for all of the targets was 100 pM, and a 4 µA constant current was applied.

Figure 8:
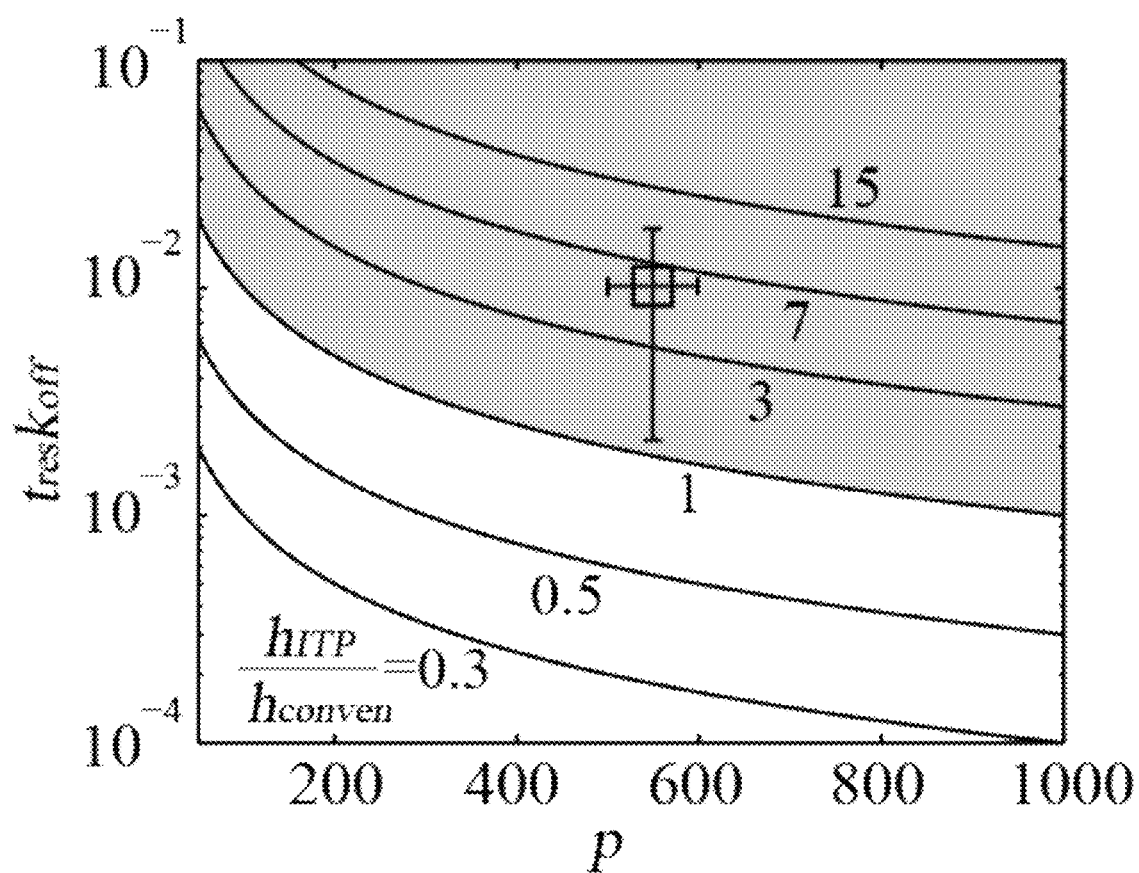

FIG. 8 shows contours representing the ratio of fraction of hybridized probes of ITP hybridization to that of conventional hybridization. We obtained the curves using $C_0^* = 10^{-4}$, but we observed negligible change for $C_0^* < 10^{-2}$. The gray area represents the range of parameters, $t_{res}k_{off}$ and p, with which ITP yields higher sensitivity over the conventional method. The square symbol represents the experimental condition (p=549, $t_{res}$=235 s, and $k_{off}$=4.3×10$^{-4}$ s$^{-1}$) we used in the titration experiment presented in the later section. The theoretical prediction of sensitivity increase for the case is calculated as 5.6. The uncertainty bar represents 95% confidence intervals for the fitting parameter and experimental measurements.

Figure 9:
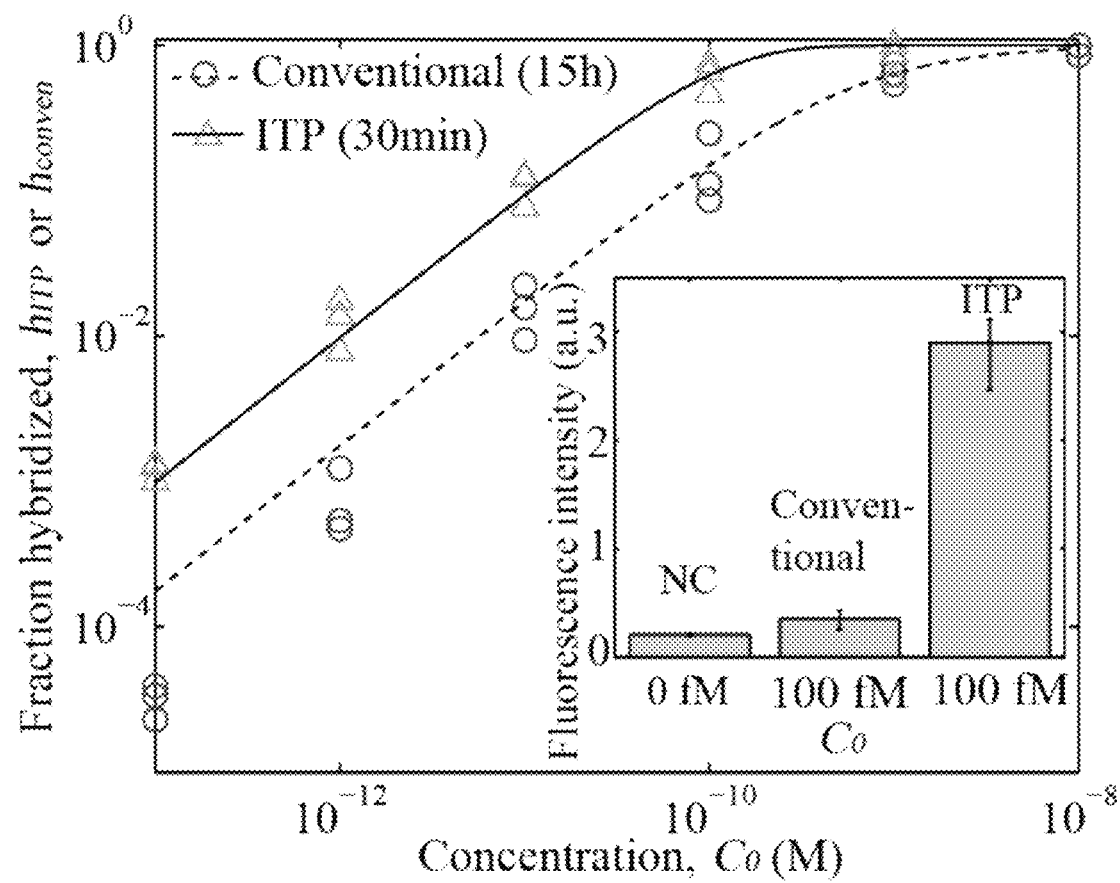

FIG. 9 shows experimental data demonstrating quantitative and sensitive detection of a target sequence using ITP microarray hybridization. Titration curves were obtained for 26 nucleotide ssDNA (target 1) concentrations ranging from 100 fM to 10 nM. Along with experimental data (symbols), we show results of analytical models with a respective fitting parameter for ITP (solid) and conventional (dashed) hybridization. Inset compares fluorescence intensity from $C_0$=100 fM hybridization data of both methods and the negative control with no target. The fluorescence intensity from each method divided by the negative control was 1.7 for conventional and 14 for ITP hybridization, corresponding to an 8.2-fold increase in sensitivity for a 30 minute ITP hybridization. The range bar was used to indicate maximum and minimum data points (N=3).

Figure 10:
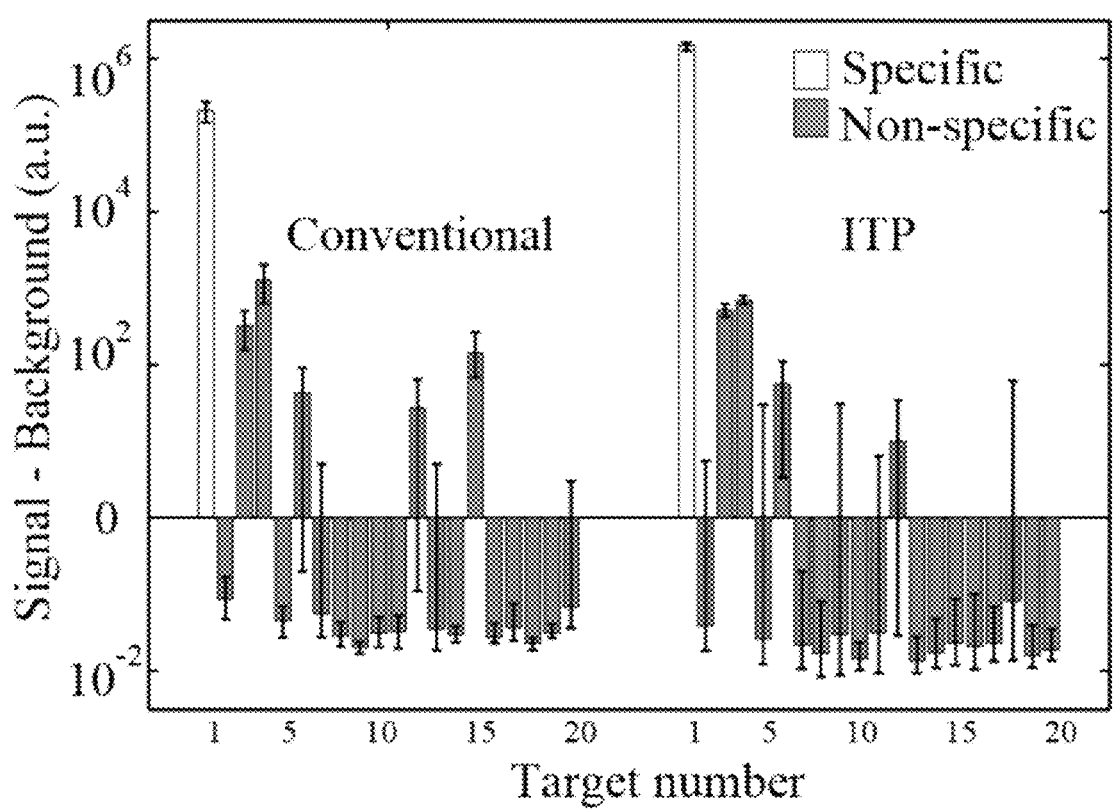

FIG. 10 shows a comparison of specific and nonspecific signal between conventional and ITP hybridization. We hybridized sample including 100 pM target 1 alone, and measured fluorescence intensity from 20 probe sequences. Data shown is the average intensity from three experiments with range bars representing the absolute range of measured values. Negative value of the background-subtracted intensity indicates non-specific binding was not observed. Ratio of the specific signal to the highest nonspecific signal was 160 for conventional, and 2130 for ITP hybridization.

DETAILED DESCRIPTION

The practice of the present invention will employ, unless otherwise indicated, conventional methods of chemistry, biochemistry, cell biology, molecular biology and recombinant DNA techniques, within the skill of the art. Such techniques are explained fully in the literature. See, e.g., M. Schena *Microarray Analysis* (Wiley-Liss, 2002); *Microarrays: Principles, Applications and Technologies* (J. V. Rogers ed., Nova Science Pub. Inc., 2014); A. K. Mallia, P. K. Smith, G. T. Hermanson *Immobilized Affinity Ligand Techniques* (Academic Press; 1$^{st}$ edition, 1992); *Affinity Chromatography: Methods and Protocols* (Methods in Molecular Biology, P. Bailon ed., Humana Press; 1$^{st}$ edition, 2000); T. K. Khurana *On-chip isotachophoresis assays for high sensitivity electrophoretic preconcentration, separation, and indirect detection* (ProQuest, UMI Dissertation Publishing, 2011); F. M. Everaerts, J. L. Beckers *Isotachophoresis Theory, Instrumentation and Applications* (Journal of chromatography library, Volume 6, Elsevier Science Ltd., 1976); A. L. Lehninger, *Biochemistry* (Worth Publishers, Inc., current addition); Sambrook et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a reactant" includes a mixture of two or more reactants, and the like.

The terms "polynucleotide," "oligonucleotide," "nucleic acid" and "nucleic acid molecule" are used herein to include a polymeric form of nucleotides of any length, either ribonucleotides or deoxyribonucleotides. These terms refer only to the primary structure of the molecule. Thus, triple-, double- and single-stranded DNA, as well as triple-, double- and single-stranded RNA are included. Modifications, such as by methylation, polyadenylation, and/or by capping, and unmodified forms of the polynucleotide are also included.

As used herein, the term "ligand" refers to a molecule that binds to another molecule, e.g., an antigen binding to an antibody, a hormone or neurotransmitter binding to a receptor, a substrate or allosteric effector binding to an enzyme, or a carbohydrate binding to a lectin, and includes natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

The terms "affinity ligand" and "affinity molecule" are used interchangeably herein and refer to a molecule that will selectively bind, through chemical or physical means to a substance present in a sample. By "selectively bind" is meant that the molecule binds preferentially to the target of interest or binds with greater affinity to the target than to other molecules. For example, a DNA molecule will bind to a substantially complementary sequence and not to unrelated sequences. An oligonucleotide that "specifically binds" to a particular nucleic acid, denotes an oligonucleotide, e.g., a probe, primer, or capture oligonucleotide that binds to the particular nucleic acid, but does not bind to other nucleic acids.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity ligand" and "target analyte" are used herein to refer to first and second members of a binding pair, respectively.

As used herein, the term "probe" or "nucleic acid probe" refers to a polynucleotide, as defined above, that contains a nucleic acid sequence complementary to a nucleic acid sequence present in a target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. A probe may be used to "capture" the target nucleic acid. One or more probes can be used in order to capture the target nucleic acid. Typically, a probe used to capture a target nucleic acid is associated with a solid support, either directly or indirectly.

The terms "hybridize" and "hybridization" refer to the formation of complexes between nucleotide sequences which are sufficiently complementary to form complexes via Watson-Crick base pairing. For example, a nucleic acid probe immobilized on a solid support "hybridizes" with a target (e.g., nucleic acid analyte from a sample) to form a complex (or hybrid), thus capturing the target.

It will be appreciated that hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

By "isolated" is meant, when referring to a polypeptide or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "label" and "detectable label" refer to a molecule capable of detection, including, but not limited to, radioactive isotopes, stable (non-radioactive) heavy isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to radiolabels (e.g., $^3$H, $^{125}$I, $^{35}$S, $^{14}$C, or $^{32}$P), stable (non-radioactive) heavy isotopes (e.g., $^{13}$C or $^{15}$N), phycoerythrin, fluorescein, 7-nitrobenzo-2-oxa-1,3-diazole (NBD), YPet, CyPet, Cascade blue, allophycocyanin, Alexa dyes (e.g., Alexa 350, Alexa 430, Alexa 488, Alexa 532, Alexa 546, Alexa 555, Alexa 594, Alexa 647, Alexa 660, Alexa 680, and Alexa 750), Atto dyes (e.g., Atto 488, Atto 532, Atto 550, Atto 565, Atto 590, Atto 610, Atto 620, Atto 635, Atto 647, Atto 655, and Atto 680), Cy3, Cy5, Cy7, TYE 563, TYE 665, TYE 705, TEX 615, JOE, TET, HEX, TAMRA, ROX, rhodamine, dansyl, umbelliferone, Texas red, luminol, acradimum esters, biotin or other streptavidin-binding proteins, magnetic beads, electron dense reagents, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mApple, mCherry, rsCherry, rsCherryRev, firefly luciferase, Renilla luciferase, NADPH, beta-galactosidase, horseradish peroxidase, glucose oxidase, alkaline phosphatase, chloramphenical acetyl transferase, and urease. Enzyme tags are used with their cognate substrate. As with many of the standard procedures associated with the practice of the invention, skilled artisans will be aware of additional labels that can be used.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "array" refers to a population of different reaction sites, which can be present on one or more supports, such that the different reaction sites can be differentiated from each other according to their relative location. Typically, a single molecular species (e.g., probe) is attached at each individual reaction site. However, multiple copies of a particular molecular species can be attached at a particular reaction site. The array taken as a whole will typically include a plurality of different molecular species attached at a plurality of different sites. The reaction sites can be located at different addressable locations on the same support. Alternatively, an array can include separate supports, such as beads, each bearing different reaction sites.

As used herein, a "solid" or "solid support" refers to a solid surface, such as, but not limited to a plate, slide, wafer, bead, rod, particle, strand, disc, membrane, film, or the inner surface of a tube, channel, column, flow cell device, or microfluidic device. A solid may comprise various materials, including, but not limited to glass, quartz, silica, metal, ceramic, plastic, nylon, polyacrylamide, resin, porous polymer monolith, hydrogel, and composites thereof. Additionally, a substrate may be added to the surface of a solid to facilitate attachment of a reactant (e.g., affinity ligand or nucleic acid probe).

The term "electroosmotic flow" refers to the motion of liquid induced by an applied potential across a porous material, capillary tube, microchannel, or other fluid conduit.

The term "about," particularly in reference to a given quantity, is meant to encompass deviations of plus or minus five percent.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention relates to devices and methods for controlling reversible chemical reactions at solid-liquid interfaces by concentrating a reactant in a liquid phase in the vicinity of another reactant on the surface of a solid to increase their rate of reaction and replacing the liquid phase with an immiscible phase, such as an immiscible gas or liquid that inhibits the reverse reaction. In particular, the inventors used isotachophoresis to preconcentrate a target molecule in a liquid phase in the region of a reactant or ligand immobilized on the surface of a solid followed by removal of the liquid phase and replacement with a gas that impeded the reverse reaction. In Examples 1 and 2, the inventors describe using this method for increasing the rates and degree of completion of kinetically limited nucleic acid hybridization reactions. The inventors further describe exemplary devices for performing ITP in combination with either affinity chromatography (Example 1) or microarray analysis (Example 2).

In order to further an understanding of the invention, a more detailed discussion is provided below regarding devices and methods for increasing the rates and degree of completion of chemical reactions at solid-liquid interfaces.

In one embodiment, isotachophoresis is combined with phase replacement to enhance the rates and degree of completion of chemical reactions at solid-liquid interfaces. First, isotachophoresis is performed on a liquid sample containing a first reactant to concentrate it in the vicinity of a second reactant immobilized on the surface of a solid. ITP is performed on the contents of the sample with trailing and leading electrolytes that are selected such that the reactant in the liquid sample focuses at the TE-LE interface. Preferably, the TE and LE are chosen such that contaminating species in the sample have electrophoretic mobilities either smaller than the trailing ion or larger than the leading ion and are not focused at the TE-LE interface with the reactant. After carrying out the reaction, the reverse reaction is impeded by removal of the liquid and replacement of the liquid with a gas or an immiscible liquid that inhibits the reverse reaction.

In certain embodiments, ITP is performed with the LE and TE in solution at a pH between 4 and 10. Electrolytes may include, but are not limited to TRIS and HCl as the LE or 6-aminocaproic acid and HCl as the LE, HEPES and TRIS as the TE, HEPES and BIS-TRIS as the TE, HEPES and histadine as the TE, MES and TRIS as the TE, MES and BIS-TRIS as the TE, MES and histadine as the TE, caproic acid and TRIS as the TE, caproic acid and BIS-TRIS as the TE, caproic acid and histadine as the TE, and caproic acid and β-alanine as the TE. The concentrations of ions and buffers can be adjusted to provide the appropriate effective mobility. In addition, an agent for suppressing electroosmotic flow may be added such as, but are not limited to polylactams (e.g., polyvinylpyrrolidone), substituted polyacrylamide derivatives, water soluble methylhydroxyethyl derivatives of cellulose, polyvinylalcohol, polyvinylpyrrolidones, and polyethyleneglycols. Exemplary LE and TE solutions include an LE solution containing 250 mM HCl and 500 mM TRIS and a TE solution containing 25 mM HEPES and 50 mM TRIS (see Example 1), and an LE solution containing 250 mM HCl, 500 mM TRIS, 5 mM $MgCl_2$, 0.1% w/w poly(vinylpyrrolidone) (PVP), 10% formamide, and 0.01% w/w Tween 20 or an LE gel containing 250 mM HCl, 500 mM TRIS, and 25% w/v Pluronic F-127 and a TE solution containing 25 mM HEPES, 50 mM BIS-TRIS, and 1% PVP (see Example 2).

In certain embodiments, this method is used to accelerate the reaction of two reactants that specifically bind to each other (i.e., binding pair). "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Examples of binding pairs include, but are not limited to, complementary polynucleotides capable of hybridization to form nucleic acid duplexes, a receptor that binds a hormone, agonist, or antagonist, an antibody that binds an antigen, an enzyme that binds a substrate, inhibitor, activator, or cofactor, and a lectin that binds a carbohydrate.

In one embodiment, the reaction accelerated by the methods of the invention is a nucleic acid hybridization reaction. For nucleic acid hybridization reactions, one or more additives or enhancing agents may be included to improve hybridization, for example, by reducing secondary structure in a nucleic acid. Such additives or enhancing agents include, but are not limited to, dimethyl sulfoxide (DMSO), N,N,N-trimethylglycine (betaine), formamide, glycerol, nonionic detergents (e.g., Triton X-100, Tween 20, and Nonidet P-40 (NP-40), 250 mM HCl, 500 mM TRIS, and 25% w/v Pluronic F-127), 7-deaza-2'-deoxyguanosine, bovine serum albumin, T4 gene 32 protein, polyethylene glycol, 1,2-propanediol, and tetramethylammonium chloride.

In certain embodiments, ITP is combined with affinity chromatography according to the methods of the invention. In this case, the first reactant is an analyte of interest in a liquid sample and the second reactant is an affinity ligand immobilized on the surface of a solid. ITP is used to preconcentrate the analyte of interest in the vicinity of the affinity ligand to increase the rate of association. After binding of the analyte, removal of liquid impedes dissociation of the analyte from the affinity ligand.

Figure 1A:
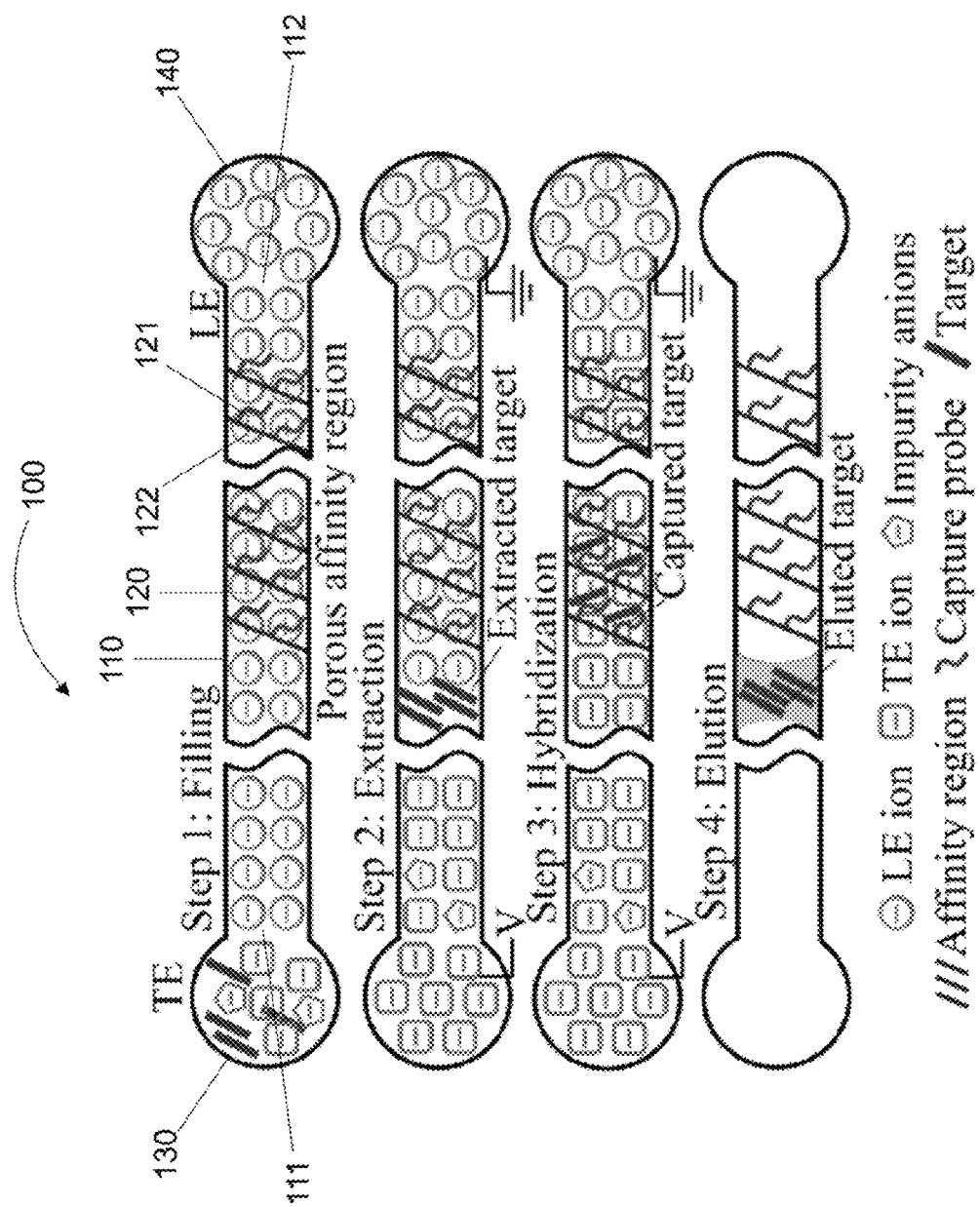
FIGS. 1A-1C.

In one aspect, the invention includes a device 100 for performing ITP in combination with affinity chromatography, the device comprising: a) a tube 110 comprising an input end 111 and an output end 112; b) an affinity region 120 comprising a plurality of affinity ligands 121 immobilized on a solid support 122, wherein the affinity region is located inside the tube 110; c) a first reservoir 130 comprising the TE, wherein the first reservoir is connected to the input end 111 of the tube 110; and d) a second reservoir 140 comprising the LE, wherein the second reservoir is connected to the output end 112 of the tube 110 (see FIG. 1A).

Affinity chromatography is performed with such a device by filling the second reservoir and the tube with a solution comprising the LE. A sample comprising a target molecule and the TE is added to the first reservoir. ITP is performed on the sample such that the target molecule is concentrated at an LE-TE interface in the affinity region, where the target molecule is captured by binding to an affinity ligand. The solutions comprising the LE and the TE are then removed to impede dissociation of the target molecule from the affinity ligand. Finally, the target molecule is eluted.

The tube may be a capillary, a chromatography column, or a microfluidic channel within a microfluidic device. In one embodiment, the tube is composed of a non-conducting material, such as silicate or borosilicate. The tube may be treated for electroosmotic flow suppression or for other beneficial flow modifying effects. For example, the tube may be pretreated with one or more agents including silanizing agents, alcohols, acids, or water. Preferably, the affinity region has a hydrodynamic resistance low enough to allow the tube to be filled without the use of a high pressure pump.

The affinity region may comprise any type of suitable affinity chromatography media. Conventional affinity chromatography media typically include particulate sorbents, such as beads or resin comprising covalently attached affinity ligands capable of binding the target analyte of interest. Exemplary solid supports for affinity chromatography may comprise polyether sulfone, agarose, cellulose, a polysaccharide, polytetrafluoroethylene, polysulfone, polyester, polyvinylidene fluoride, polypropylene, poly(tetrafluoroethylene-co-perfluoro(alkyl vinyl ether)), polycarbonate, polyethylene, glass, polyacrylate, polyacrylamide, poly(azolactone), polystyrene, polydivinylbenzene, polylactide, ceramic, nylon or metal. The affinity chromatography matrix may further comprise a linking group, such as, but not limited to, cyanogen bromide, tresyl, triazine, vinyl sulfone, an aldehyde, an epoxide, or an activated carboxylic acid to facilitate coupling of the affinity reagent to the solid support. The chromatography matrix can be prepared by coupling the affinity ligand to the solid support with the linking group by chemically activating the solid support if necessary, and contacting the solid support with the affinity ligand such that the affinity ligand covalently attaches to the solid support. Additionally, the affinity ligand may be connected to the solid support through a linker to make the affinity ligand more accessible for binding to the target analyte. See, e.g., A. K. Mallia, P. K. Smith, G. T. Hermanson Immobilized Affinity Ligand Techniques (Academic Press; 1st edition, 1992); Affinity Chromatography: Methods and Protocols (Methods in Molecular Biology, P. Bailon ed., Humana Press; 1st edition, 2000), Guide to Protein Purification (Methods in Enzymology Vol. 182, M. P. Deutcher ed., Academic Press, Inc.); herein incorporated by reference in their entireties.

Alternatively, the affinity region may comprise a porous polymer monolith. An advantage of using porous polymer monoliths is that separations can be carried out at higher flow rates than with conventional affinity media, which allows purification to be accomplished in a shorter amount of time. Porous polymer monoliths are produced by polymerization of organic monomers with crosslinkers in the presence of a porogenic solvent or pore-forming reagent. The porous polymer monolith is prepared in a mold, typically a tube or fluidic channel (e.g. a capillary, column, or microfluidic channel), which is filled with the polymerization mixture. Polymerization is initiated by heating or UV light. For a review of porous polymer monoliths and methods of preparing and using them in chromatographic applications, see, e.g., Xie et al. (2002) Adv. Biochem. Eng. Biotechnol. 76:87-125; Potter et al. (2008) J. Sep. Sci. 31:1881-1906; and Svec (2010) J. Chromatogr. A 1217(6): 902-924; herein incorporated by reference.

In preparing porous polymer monoliths, a wide variety of monomers can be used in polymerization, including, but not limited to acrylates, methacrylates, vinylpyridines, vinylpyrrolidone, vinylbenzene, divinylbenzene, and vinyl acetate. Methacrylate and acrylate monoliths, the most commonly used, are synthesized by free radical UV-initiated copolymerization of functional monomers with a crosslinking agent, such as ethylene glycol dimethacrylate (EDMA) or trimethyloylpropane trimethacrylate (TRIM). Examples of porous methacrylate monoliths include glycidyl methacrylate (GMA), butyl methacrylate (BuMA), 2-aminoethyl methacrylate (AEMA), 2-hydroxyethyl methacrylate (HEMA), and 2-cyanoethyl methacrylate (CEMA) (see, e.g., Maksimova et al. (2011) J. Chromatogr. A 1218(17):2425-2431; Vlakh E G, Tennikova T B. (2007) J. Sep. Sci. 30(17):2801-2813; herein incorporated by reference in their entireties).

Monoliths with immobilized affinity ligands can be prepared in a variety of ways. For example, in GMA-based monoliths, the reactivity of the surface epoxide group facilitates covalent attachment of affinity ligands. The epoxide group can be reacted with a nucleophile on the affinity ligand, such as an amine. If desired, the epoxide group may be modified to introduce a spacer arm (see, e.g., Pflegerl et al. (2002) J. Comb. Chem. 4:33-37; Mallik et al. (2006) J. Sep. Sci., 29:1686-1704; Josic et al. (2007) Chromatogr. A 1144: 2-13; Josic et al. (2001) J. Biochem. Biophys. Methods, 49:153-174; Platonova et al. (2005) J. Chromatogr. A 1065:19-28; herein incorporated by reference in their entireties).

In other embodiments, ITP is combined with microarray analysis according to the methods of the invention. In this case, the first reactant is a nucleic acid analyte of interest in a liquid sample and the second reactant is a nucleic acid probe of a microarray. ITP is used to preconcentrate the nucleic acid analyte of interest in the vicinity of the microarray to increase its rate of hybridization. After binding of the nucleic acid analyte, removal of liquid impedes dissociation of the nucleic acid analyte from the probe of the microarray.

In one aspect, the invention includes a device 200 for performing ITP in combination with microarray analysis, the device comprising: a) a microarray 220 comprising a plurality of nucleic acid probes immobilized on a solid support; b) a fluidic channel 210 containing the microarray, wherein the fluidic channel comprises an input end 211 and an output end 212 and a constriction 213 located between the input end and the microarray 220; c) a first reservoir 230 comprising the TE, wherein the first reservoir is connected to the input end of the fluidic channel; and d) a second reservoir 240 comprising the LE, wherein the second reservoir is connected to the output end of the fluidic channel (see FIG. 7A). In certain embodiments, the fluidic channel 210 is a capillary or a microfluidic channel within a microfluidic device.

Microarray analysis is performed with such a device by filling the fluidic channel with a solution comprising the LE and the second reservoir with a gel comprising the LE. A sample comprising target nucleic acids and the TE is added to the first reservoir. Isotachophoresis (ITP) is carried out until the LE-TE interface reaches the constriction. Then, the electric field is turned off for a period of time sufficient to allow the nucleic acids to distribute across a cross-section of the fluidic channel by diffusion. Next, a low electric field is applied such that target nucleic acids concentrated over the microarray hybridize to the nucleic acid probes of the microarray while unbound nucleic acids continue to migrate downstream of the microarray. Hybridization to the microarray probes can be detected by any suitable method. Typically, nucleic acids in the sample are labeled with a detectable label, for example, with a fluorophore or other label, to facilitate detection of hybridization.

Microarrays can be made by any method known in the art. In general, microarrays are prepared by immobilizing nucleic acid probes to a solid support or surface. The probes may comprise, for example, DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Probes used in the methods of the invention are preferably attached to a solid support, which may be either porous or non-porous. The solid support or surface may be made, for example, from glass, plastic (e.g., polypropylene, nylon), polyacrylamide, nitrocellulose, gel, or other porous or non-porous material. One method for attaching nucleic acids to a surface is by printing on glass plates, as is described generally by Schena et al, Science 270:467-470 (1995). This method is especially useful for preparing microarrays of cDNA (See also, DeRisi et al, Nature Genetics 14:457-460 (1996); Shalon et al., Genome Res. 6:639-645 (1996); and Schena et al., Proc. Natl. Acad. Sci. U.S.A. 93:10539-11286 (1995); herein incorporated by reference in their entireties).

A second method for making microarrays produces high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; herein incorporated by reference in their entireties) or other methods for rapid synthesis and deposition of defined oligonucleotides (Blanchard et al., Biosensors & Bioelectronics 11:687-690; herein incorporated by reference in its entirety). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, Nuc. Acids Res. 20:1679-1684; herein incorporated by reference in its entirety), may also be used. In principle, any type of array, for example, dot blots on a nylon hybridization membrane (see Sambrook, et al., *Molecular Cloning: A Laboratory Manual*, 3$^{rd}$ Edition, 2001) could be used. However, as will be recognized by those skilled in the art, very small arrays will frequently be preferred because hybridization volumes will be smaller.

Microarrays can also be manufactured by means of an ink jet printing device for oligonucleotide synthesis, e.g., using the methods and systems described by Blanchard in U.S. Pat. No. 6,028,189; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123; herein incorporated by reference in their entireties. Specifically, the oligonucleotide probes in such microarrays are synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 cm$^2$. The polynucleotide probes are attached to the support covalently at either the 3' or the 5' end of the polynucleotide.

As noted above, the "probe" to which a particular polynucleotide molecule specifically hybridizes contains a complementary polynucleotide sequence. The probes of the microarray typically consist of nucleotide sequences of no more than 1,000 nucleotides. In some embodiments, the probes of the array consist of nucleotide sequences of 10 to 1,000 nucleotides. In one embodiment, the nucleotide sequences of the probes are in the range of 10-200 nucleotides in length and are genomic sequences of one species of organism, such that a plurality of different probes is present, with sequences complementary and thus capable of hybridizing to the genome of such a species of organism, sequentially tiled across all or a portion of the genome. In other embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, or are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone (e.g., phosphorothioates).

In one embodiment, the microarray comprises a support or surface with an ordered array of binding (e.g., hybridization) sites or "probes" for binding analytes of interest. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). Each probe is preferably covalently attached to the solid support at a single site.

Generally, microarrays are reproducible, allowing multiple copies of a given array to be produced and easily compared with each other. Preferably, microarrays are made from materials that are stable under binding (e.g., nucleic acid hybridization) conditions. Microarrays are generally small, e.g., between 1 cm$^2$ and 25 cm$^2$; however, larger arrays may also be used, e.g., in screening arrays. Preferably, a given binding site or unique set of binding sites in the microarray will specifically bind (e.g., hybridize) to the product of a single gene in a cell (e.g., to a specific mRNA or to a specific cDNA derived therefrom). However, in general, other related or similar sequences will cross hybridize to a given binding site.

As mentioned above, nucleic acids in a sample may be labeled to facilitate detection of hybridization. Any method known in the art may be used to label nucleic acids. Nucleic acids can be detectably labeled at one or more nucleotides. Preferably, this labeling incorporates the label uniformly along the length of the nucleic acid, and more preferably, the labeling is carried out at a high degree of efficiency. For example, polynucleotides can be labeled by oligo-dT primed reverse transcription. Random primers (e.g., 9-mers) can be used in reverse transcription to uniformly incorporate labeled nucleotides over the full length of the polynucleotides. Alternatively, random primers may be used in conjunction with PCR methods or T7 promoter-based in vitro transcription methods in order to amplify polynucleotides.

The detectable label may be a luminescent label. For example, fluorescent labels, bioluminescent labels, chemiluminescent labels, and colorimetric labels may be used in the practice of the invention. Fluorescent labels that can be used include, but are not limited to, fluorescein, a phosphor, a rhodamine, or a polymethine dye derivative. Additionally, commercially available fluorescent labels including, but not limited to, fluorescent phosphoramidites such as FluorePrime (Amersham Pharmacia, Piscataway, N.J.), Fluoredite (Miilipore, Bedford, Mass.), FAM (ABI, Foster City, Calif.), and Cy3 or Cy5 (Amersham Pharmacia, Piscataway, N.J.) can be used. Alternatively, the detectable label can be a radiolabeled nucleotide.

Nucleic acid hybridization and wash conditions are chosen so that the target polynucleotide molecules specifically bind or specifically hybridize to the complementary polynucleotide sequences of the array, preferably to a specific array site, wherein its complementary DNA is located. Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (3rd Edition, 2001), and in Ausubel et al., *Current Protocols In Molecular Biology*, vol. 2, Current Protocols Publishing, New York (1994). Typical hybridization conditions for the cDNA microarrays of Schena et al. are hybridization in 5.times.SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., Proc. Natl. Acad. Sci. U.S.A. 93:10614 (1993)). Useful hybridization conditions are also provided in, e.g., Tijessen, 1993, *Hybridization with Nucleic Acid Probes*, Elsevier Science Publishers B. V.; and Kricka, 1992, *Nonisotopic DNA Probe Techniques*, Academic Press, San Diego, Calif. Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," Genome Research 6:639-645, which is incorporated by reference in its entirety for all purposes). Arrays can be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., Genome Res. 6:639-645 (1996), and in other references cited herein. Alternatively, the fiber-optic bundle described by Ferguson et al., Nature Biotech. 14:1681-1684 (1996), may be used to monitor mRNA abundance levels at a large number of sites simultaneously.

In yet another aspect, the invention provides kits for increasing the rates and degree of completion of chemical reactions at solid-liquid interfaces according to the methods described herein. The kit may include one or more agents for performing ITP (e.g., electrolytes, buffers, and electrodes), a solid support with at least one immobilized reactant, and a gas or immiscible liquid to be used for phase replacement. The kit may further provide printed instructions for carrying out ITP and phase replacement in order to enhance the rate and degree of completion of a chemical reaction. The kit can comprise one or more containers for compositions and devices contained in the kit. Suitable containers for the compositions include, for example, bottles, vials, syringes, and test tubes. Containers can be formed from a variety of materials, including glass or plastic. The agents and devices may be packaged in separate containers.

In one embodiment, the kit contains a device for performing ITP in combination with affinity chromatography, as described herein, and printed instructions for carrying out ITP in combination with affinity chromatography. The kit may further comprise reagents for performing affinity chromatography.

In another embodiment, the kit contains a device for performing ITP in combination with microarray analysis, as described herein, and printed instructions for carrying out ITP in combination with microarray analysis. The kit may further comprise reagents for performing microarray analysis.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Coupling Isotachophoresis with Affinity Chromatography for Rapid, Selective Purification with High Column Utilization We used ITP to preconcentrate target analytes prior to affinity chromatography (AC) in order to accelerate the reaction between a target analyte and a stationary phase resulting in capture and enrichment of the target analyte. In particular, we combined ITP and AC in a porous polymer monolith (PPM) functionalized with a synthetic cDNA ligand. This approach (a) drastically reduced assay time; (b) improved column utilization; (c) allowed for capture of targets with higher dissociation constants; (d) obviated the need for high pressure specialized pumps; (e) directly integrated an automatic wash step into the process, eliminating a separate wash step; and (f) reduced affinity substrate fouling (and competing reactions) by partially separating sample compounds by their electrophoretic mobility. Further, the use of a PPM with approximately 1 micron pores enabled ITP selective focusing and transport of a large macromolecule (DNA). The latter can be difficult with nanoporous gels (e.g., polyacrylamide) which, in our experience, can reduce the mobility of target macromolecules to the degree that selective ITP purification is difficult (Marshall et al. (2014) J. Chromatogr. A. 1331:139-142; Swerdlow et al. (1992) Electrophoresis 13:475-483). In this study, we present a theoretical study and model of the dynamics of binding of an ITP-focused target to a stationary ligand species and controlled experiments using idealized synthetic targets. We here chose a synthetic oligonucleotide DNA for these studies and demonstrations as nucleic acids are important clinical markers that often require rapid purification prior to analysis (Schwarzenbach et al. (2011) Nat. Rev. Cancer 11:426-437; Wilson (1997) Appl. Environ. Microbiol. 63: 3741-3751; Boom et al. (1990) J. Clin. Microbiol. 28:495-503). To demonstrate this technique we used a microfluidic system consisting of UV-polymerized PPM in a borosilicate glass capillary with a 500 µm inner diameter.

We begin by describing the principle of coupling ITP preconcentration and AC purification. We then present an analytically solvable one-dimensional transport model for coupling of ITP with a semi-infinite AC porous column and second order reversible reaction kinetics. Our model captures the spatiotemporal dynamics of target-probe binding in the affinity region. Using our model and controlled experiments, we explore the coupled effects of target distribution width, distribution intensity, application velocity, forward and reverse reaction constants, and probe concentration on necessary affinity region length, assay time, and capture efficiency. Our new analytical approach allows us to collapse these six independent variables down to three nondimensionalized parameters summarizing all regimes. Next, we describe our choice of the affinity substrate, poly(glycidyl methacrylate-co-ethylene dimethacrylate) (GMA-EDMA) PPM for ITPAC. We describe the synthesis of GMA-EDMA PPM and the functionalization of the PPM with DNA probes. We then describe the ITP-AC protocol and choice of buffer chemistry for ITP-AC of DNA. We present an experimental validation of our model using ITP-AC experiments with Cy5 labeled 25 nucleotide synthetic DNA target and synthetic DNA probe immobilized on the PPM. Lastly, using our technique, we demonstrate sequence specific purification of 25 nucleotide target DNA from genomic fish sperm DNA, as an example of extraction from a high abundance background (with 10,000-fold greater mass than the sample).

2. Concept and Theory 2.1 Method Concept

Figure 1B:
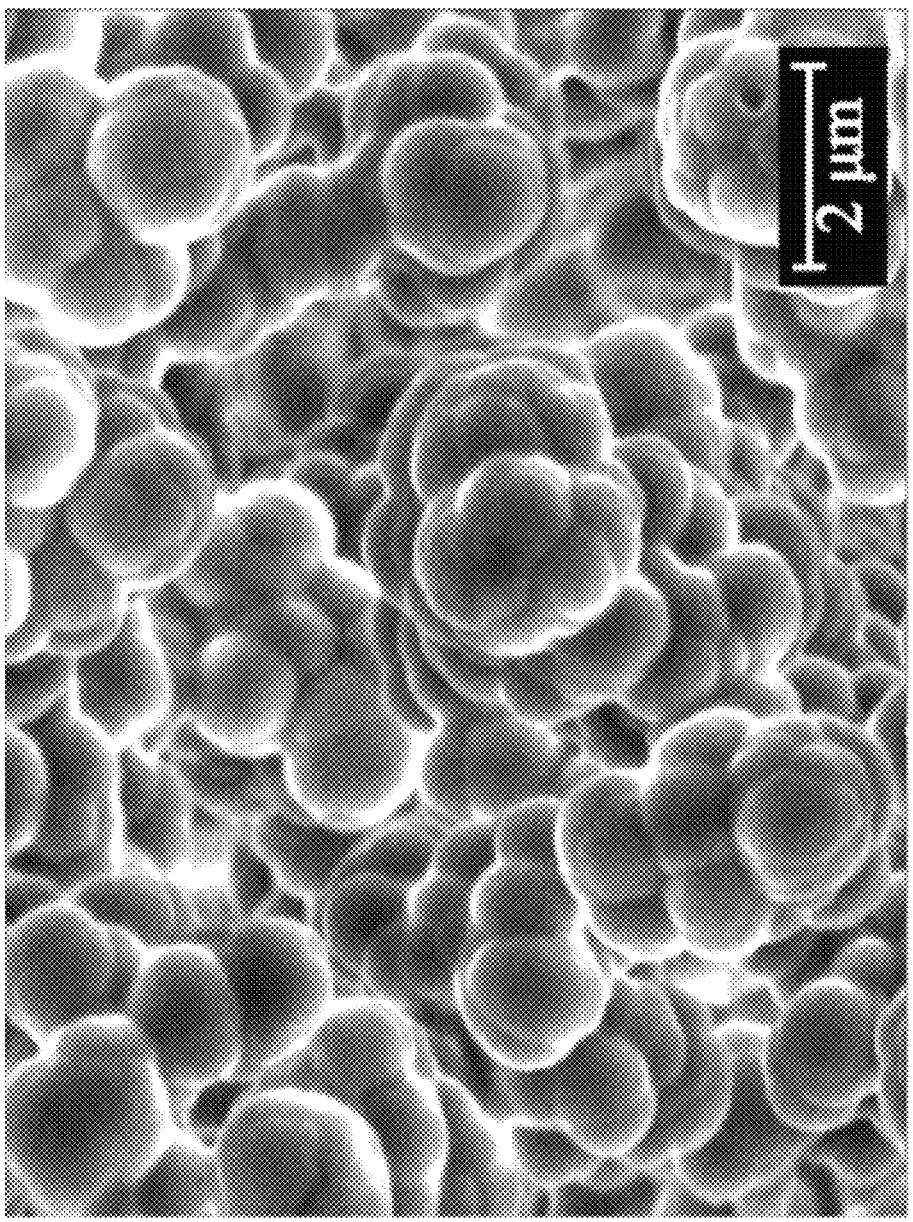

We aimed to decrease the assay time and improve affinity region utilization by purifying the target and increasing the affinity capture reaction rate. FIG. 1 summarizes the key aspects of our approach. As shown in FIG. 1A, we first fill the leading electrolyte (LE) reservoir, the capillary behind the affinity column, the porous polymer monolith affinity column (FIG. 1B), and the capillary in front of the column with LE buffer. We then mix the sample containing the target into the trailing electrolyte (TE) buffer, place this into the TE reservoir, and applied an electric field (FIG. 1A, Step 1). Under the influence of electric field, the target migrates and is concentrated at the LE-TE interface and is transported toward and reaches the affinity region (FIG. 1A, Step 2). Upon reaching the affinity region, the target reacts with the immobilized capture probe and is captured (FIG. 1A, Step 3). After capture, we inject air to remove the LE and TE from the capillary and column. We then inject a finite liquid slug (~5 µl) of elution buffer which passes through the column and elutes the target (FIG. 1A, Step 4). In the Supplementary Information (SI) (Section SI3), we provide details of our injection and ITP protocol, including an estimate of the efficiency of target extraction from the TE reservoir.

The initial focusing of ITP is selective (Marshall et al., supra) and helps prevent fouling of the affinity region by unfocused background species. The increase of the target concentration via ITP promotes faster capture reaction and the target is captured in a smaller, upstream region of the column. Exposure of the ITP-focused analyte to reaction sites on the column is temporary and is followed by a wash associated with the TE zone entering the column. We limit the time between this electrokinetic wash step (i.e., replacement with TE after capture) and the removal of liquids with air approximately 5 min or less. This approach limits the time for dissociation to occur so the captured target concentration is effectively "frozen" by the introduction of air. This enables capture of targets with significant dissociation rate.

Figure 1C:
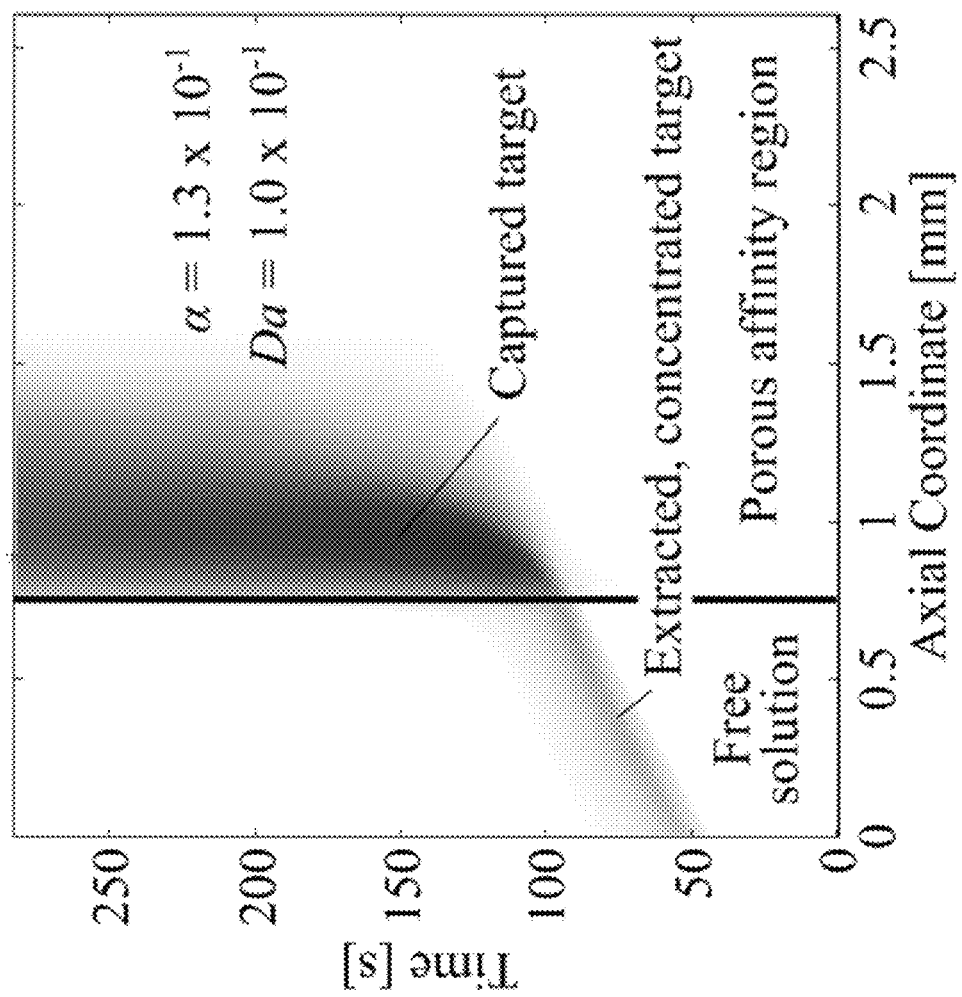

In FIG. 1C we present an experimental spatiotemporal plot of a typical ITP-aided DNA capture experiment. FIG. 1C shows Cy5 labeled target DNA binding to cDNA capture probes on the PPM affinity region. We plotted the measured cross-sectional area-averaged Cy5 labeled target fluorescence versus distance along the axis of the channel, and time. In a typical experiment the target migrates in free solution, at constant velocity, in a narrow, approximately Gaussian shaped distribution towards the affinity region. Upon reaching the affinity region, the target binds with affinity probes and persists in the affinity region. The LE, unbound molecules, and TE buffers can then be removed with air, and the target eluted with an elution buffer (not shown in FIG. 1C).

2.1 Transport of Trace Analytes in Isotachophoresis

ITP is an electrokinetic technique used to preconcentrate and separate analytes (Everaerts et al. Isotachophoresis: Theory, Instrumentation, and Applications, Elsevier, Amsterdam, New York, 1976; Bocek Analytical Isotachophoresis, VCH, Cambridge, 1987; Garcia-Schwarz et al. (2012) J. Vis. Exp. (61):e3890). We here leveraged a mode of ITP known as "peak mode" ITP where trace analytes co-focus into a relatively narrow peak at the interface of the LE and TE (Garcia-Schwarz et al. (2012), supra; Khurana et al. (2008) Anal. Chem. 80(16):6300-6307; Garcia-Schwarz et al. (2011) J. Fluid Mech. 679:455-475). In peak mode ITP, trace analytes do not appreciably contribute to local conductivity and so the peak width and analyte locations are determined by the mobilities of the ions in the system and electric field established by and at the interface between TE and LE buffers (Garcia-Schwarz et al. (2011), supra). The analyte mobility in the TE zone is higher than that the TE co-ion. The analyte mobility in the LE zone is also lower than that of the LE co-ion. This arrangement of mobilities enables purification of, for example, nucleic acids from complex mixtures and excludes possible fouling species from the ITP zone (Marshall et al., supra). If, as in our case, the analyte mobility is significantly different from that of the LE and TE ions, the target distribution is narrow and approximately Gaussian in shape (Garcia-Schwarz et al. (2011), supra).

2.2 One Dimensional Transport Reaction Model

We here present an unsteady, one-dimensional model for ITP which we will show captures the essential dynamics of the process. We chose this reduced order model in order to develop an analytical solution which identifies clearly the key governing parameters and trends of the process. We modeled focusing of an ionic target in peak mode ITP, and migrating towards a semi-infinite affinity capture region. In the affinity region, the target reacts with the surface bound probe according to a simple second-order reaction of the following form: Target+Probe⇌Target-Probe complex.

We set time at the point where the target just starts to enter the affinity region. We assumed the target had a Gaussian concentration profile with a width given by the interface width between the LE and the TE. This is a common assumption for modeling the distribution of trace analyte focused at the LE-TE interface (Bercovici et al. (2012) Proc. Natl. Acad. Sci. U.S.A. 109(28):11127-11132; Khurana et al. (2008) Anal. Chem. 80: 6300-6307; Shim et al. (2007) Heat Tr. A-Appl. 52: 441-461). As usual for peak mode ITP, we further assumed that the change in concentration of the target had no effect on the electric field in ITP (Bercovici et al., supra; Khurana et al., supra; Shim et al., supra). The target simply advects with a mean velocity u, the ITP shock propagation velocity (FIG. 1A). Our analysis showed that we can assume that diffusion of the target is negligible compared to its advection and reaction. We derived the following advection reaction equation from the general advection-diffusion reaction equation in Section SI1 of SI:

$$\frac{\partial c}{\partial t} + u\frac{\partial c}{\partial z} + k_1 c(N-n) - k_2 n = 0 \quad (1)$$

$$\frac{\partial n}{\partial t} - k_1 c(N-n) + k_2 n = 0, \quad (2)$$

where c is the concentration of the target, n is the concentration of the target bound to the probe, N is the initial concentration of probe, u is the target's velocity, and $k_1$ and $k_2$ are the forward and reverse reaction constants respectively. Equations (1) and (2) are first order accurate equations which result from an asymptotic expansion of c and n in terms of smallness parameters ε we define as $$\varepsilon \equiv \frac{u_{a,TE} - u_{a,LE-TE}}{u_{a,LE-TE}}. \quad (3)$$

Here $u_{a,TE}$ is the velocity of the analyte in the TE and $u_{a,LE-TE}$ is the velocity of the analyte in the LE-TE interface (equal to the interface velocity u) (for details see SI, Section SI1). For interested readers, we discuss in the SI (Section SI2) the second and third order accurate formulations of our problem (which are more accurate). For simplicity and emphasis, we here concentrate on the first order accurate equations as we feel they represent the simplest engineering approximation which captures the essence of the problem. We will later show that predictions from these equations agree well with measurements of key ITP-AC parameters at our experimental conditions.

Initially the affinity region is free from target, which supplies the initial condition c(z,0)=0, n(z,0)=N. We model the Gaussian profile of the ITP focused target entering the affinity region as a time varying boundary condition on the affinity region, $$c(0, t) = a \exp\left[-\left(\frac{ut - 3\sigma}{\sqrt{2}\sigma}\right)^2\right] \quad (4)$$

representing a Gaussian distribution with maximum concentration α and standard deviation σ traveling at ITP velocity u. We arbitrarily chose that at t=0, the Gaussian's maximum is 3σ to the left of the start of affinity region and therefore just beginning to interact with the affinity region. We then cast these equations along with the initial and boundary conditions in the following non-dimensionalized form:

$$\frac{\partial c^*}{\partial t^*} + \frac{\partial c^*}{\partial z^*} + \frac{\partial n^*}{\partial t^*} = 0 \quad (5)$$

$$\frac{\partial n^*}{\partial t^*} - c^*(1-n^*) + \beta n^* = 0 \quad (6)$$

$$c^*(z^*, 0) = 0 \quad (7)$$

$$n^*(z^*, 0) = 0$$

$$c^*(0, t^*) = \frac{a}{N} \exp\left[-\left(\frac{ut^*}{k_1 N \sqrt{2}\sigma} - \frac{3}{\sqrt{2}}\right)^2\right], \quad (8)$$

where $c^*$ and $n^*$ are free target and bound target concentrations normalized by initial probe concentration N, $t^*$ is time normalized by the reaction time scale $1/k_1 N$, $z^*$ is axial coordinate normalized by the advection-reaction length scale $u/k_1 N$, and $\beta = k_2/k_1 N$ is the non-dimensionalized equilibrium dissociation constant. To simplify the formulation, we introduce the following non-dimensional parameters $$\alpha = \frac{a}{N}\sqrt{2\pi} \quad (9)$$

$$Da = \frac{a\sigma k_1}{u}\sqrt{2\pi},$$

and rewrite the boundary condition as $$c^*(0, t^*) = \frac{\alpha}{\sqrt{2\pi}} \exp\left[-\frac{(\alpha/Da\, t^* - 3)^2}{2}\right]. \quad (10)$$

Here, the parameter α represents the peak concentration of the target in the Gaussian distribution scaled by the initial probe concentration N. The Damkohler number, Da as usual describes the characteristic ratio between an electrophoretic (advection) time scale and the time scale of reaction, and here is formulated as the total amount of target in the Gaussian distribution scaled by $u/k_1$. The ratio Da/α represents the width of the Gaussian distribution scaled by advection-reaction length scale $u/k_1 N$.

We analytically solved equations (5) and (6) following an approach similar to that of Thomas (J. Am. Chem. Soc. (1944) 66:1664-1666; herein incorporated by reference), but here subject to our boundary (10) and initial conditions (7). Briefly, we transformed (5) and (6) into a coordinate system moving with the ITP velocity. We then converted the result into a potential function form which collapses the two equations into a single equation. We then solved the resulting equation using Laplace transforms. We provide the solution in SI, Section SI2.

Next, we use this solution to consider the effects of non-dimensionalized target peak width, peak concentration and target-probe dissociation constant on key affinity capture parameters: capture length $p_z$, capture time $p_t$, and capture efficiency n/N.

2.3 Control of Capture Length

Figure 2A:
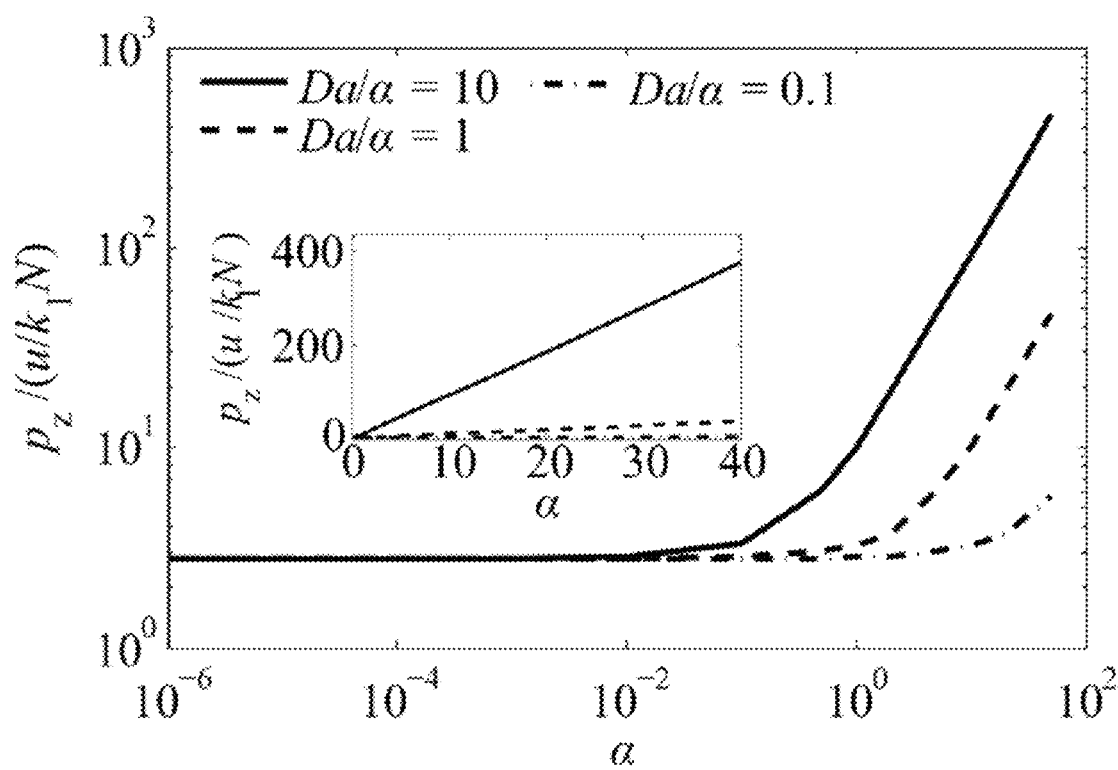
FIGS. 2A-2C shows model predictions for the (FIG. 2A) scaled capture length, (FIG. 29) scaled capture time, and (FIG. 2C) maximum capture efficiency as a function of (FIGS. 2A, 2C) scaled peak target concentration α and (FIG. 2B) scaled target distribution width Da/α for low β (plotted at $\beta=10^{-4}$). Inset in FIG. 2A shows a linear plot of scaled capture length as a function of α from 0 to 40.
Figure 2B:
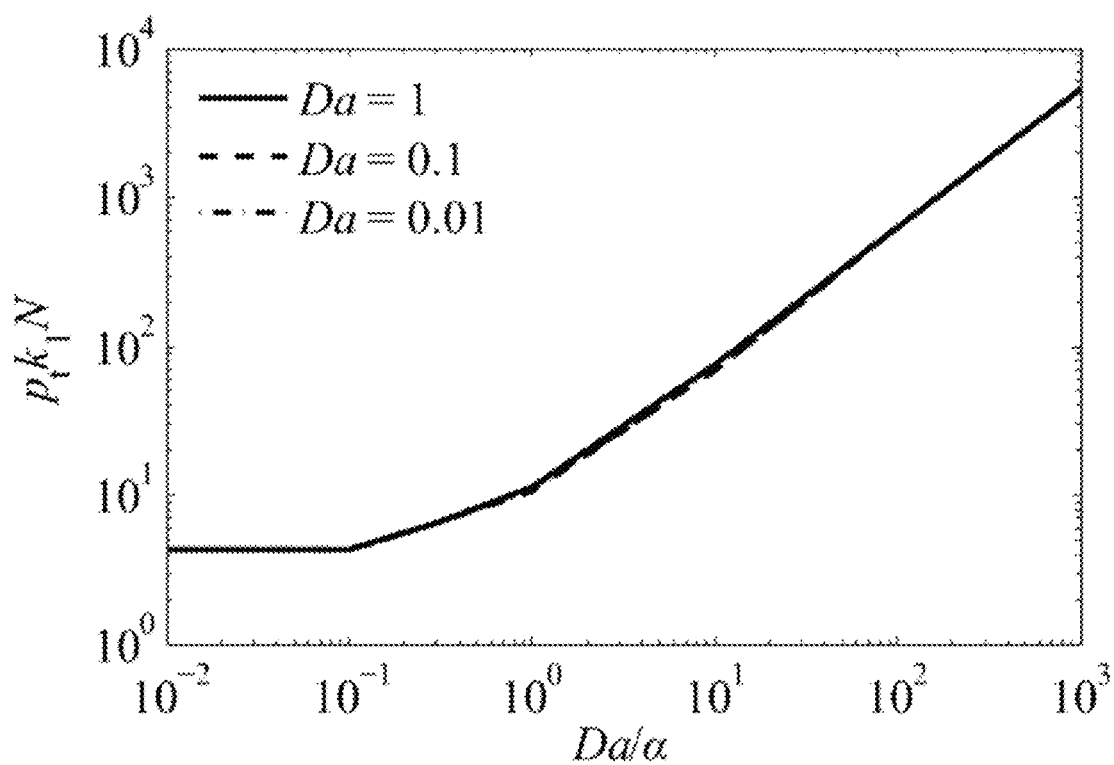
Figure 2C:
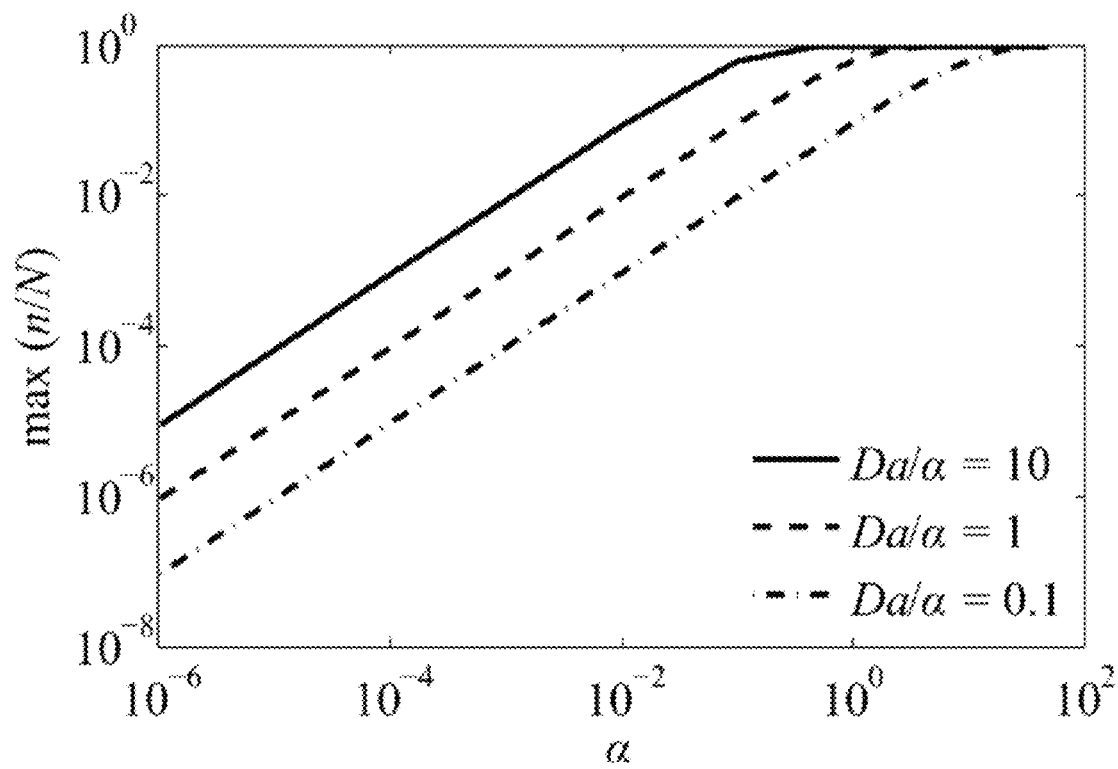
Figure 5A:
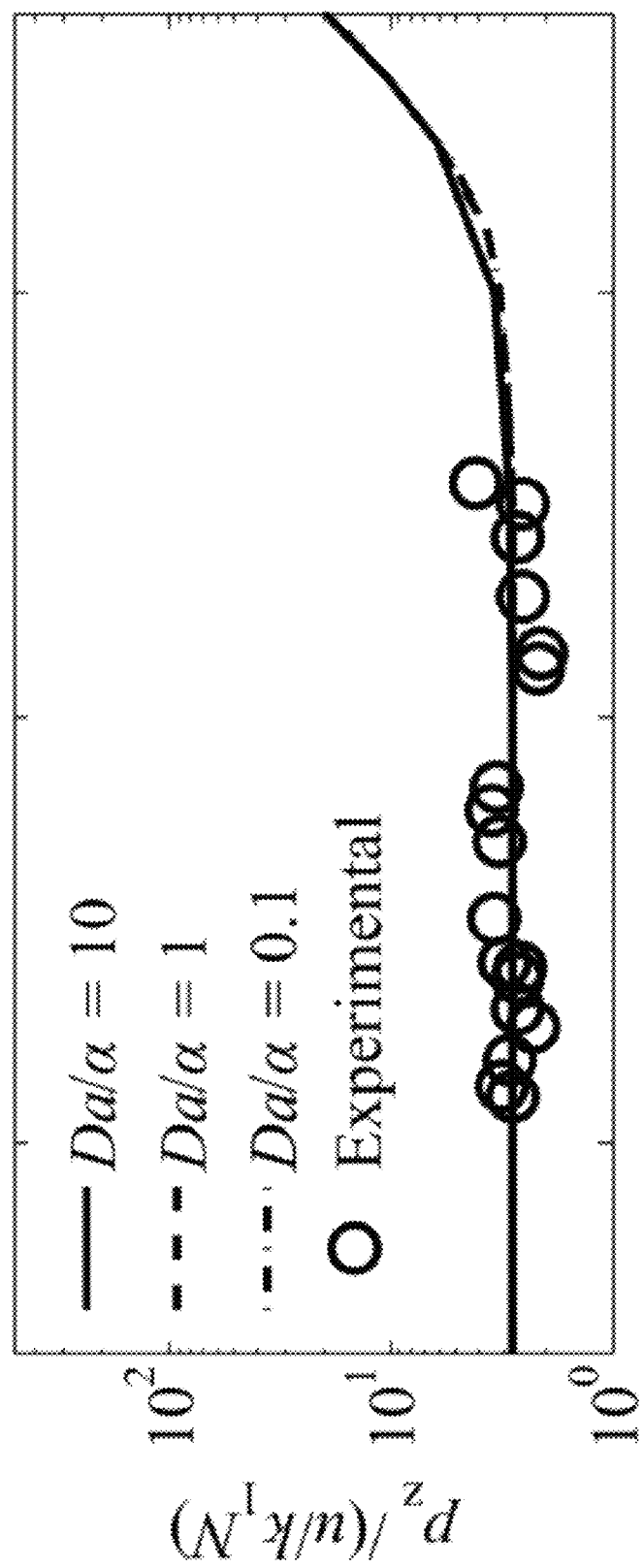
FIGS. 5A and 5B show theoretically predicted and experimentally observed (FIG. 5A) scaled capture length, and (FIG. 5B) maximum capture efficiency as a function of total scaled target amount, Da. Scaled capture length is invariant of Da for Da<1 and equals ~2.8. For Da>1, the affinity region is locally saturated and scaled capture length increases linearly with Da. Maximum capture efficiency increases linearly with Da for Da<1. For Da>1, the affinity region is locally saturated and n/N=1.

FIG. 2 summarizes the major trends between advection, reaction, and capture length and capture time scales. We here define the dimensional capture length, $p_z$, as the physical length of affinity column necessary to capture 95% of target. Inverse capture length is therefore a measure of efficiency of column utilization for columns of constant cross sectional area. $p_z$ is defined only for small values of $\beta$, where the target does not elute from the affinity region on the time scale of advecting the target through the affinity region ($\sigma/u$). We non-dimensionalize this length by the advection-reaction length scale $u/k_1 N$ and call this $p_z^*$. For Da<1 (slow reaction relative to advection), $p_z^*$ is invariant of Da (see also FIG. 5A) and approximately equals 2.8. At Da=1, the affinity region becomes locally saturated and so $p_z^*$ increases linearly with Da for Da>1. Capture length can therefore be minimized by decreasing u or increasing $k_1$ or N. Similarly, for a particular scaled target distribution width Da/α and α for which Da≤1, $p_z^*$ is invariant of α (FIG. 2A). When for a particular Da/α, a value of α gives Da=1, we term this the "critical α". For α greater than this critical α, Da>1 and so $p_z^*$ increases linearly with α as the affinity region becomes locally saturated. $p_z^*$ is invariant of scaled target distribution width Da/α (FIG. 5A).

2.4 Control of Capture Time

We define a capture time, $p_t$, as the time necessary to capture 95% of target. The capture time is proportional to the ITP-AC assay time for assays designed to capture nearly all of the target. Similar to capture length, this time is defined only for small values of β, where the target does not elute from the affinity region on the time scale of advecting the target through the affinity region. We non-dimensionalize this time by the reaction time scale $1/k_1 N$ and call this $p_t^*$. $p_t^*$ is insensitive to Da. However, we do see that $p_t^*$ increases linearly with Da/α for distribution widths greater than the advection-reaction length scale, Da/α>1 (FIG. 2B). The latter is simply because it takes proportionally more time for a wider distribution to completely enter the affinity region and be captured. For Da/α<1 the slope of $p_t^*$ decreases with decreasing Da/α and $p_t^*$ and finally asymptotes to 4.3. In this regime, σ<u $k_1 N$, and as $p_t^*$ asymptotes to 4.3, σ<<u/$k_1 N$. In this regime, the target distribution effectively acts as a Dirac delta distribution and all length and time scales are determined by reaction and advection. Interestingly, in this regime, the absolute penetration depth $p_z$ is still ≥2.8u/$k_1 N$. Therefore, in this regime, irrespective of the target distribution width, the target still travels at least 2.8u/$k_1 N$, and this travel lasts at least 4.3/$k_1 N$. This leads us to the conclusion that there is little need to decrease the target distribution width approximately below 0.1u/$k_1 N$. That is, the regime of Da/α<0.1 is sufficient to remove dependence on initial target distribution.

In traditional AC, the target is applied in a manner such that the initial condition resembles a top-hat distribution (Hage, Handbook of Affinity Chromatography, CRC Press, Boca Raton, 2006). However, for purposes of simple comparison with our technique, we can approximate the top-hat distribution with a Gaussian distribution, setting equal the width and the standard deviation respectively and the heights of the top-hat and Gaussian distributions. Therefore, application of a dilute target, for example by pressure driven flow, is represented by a wide Gaussian distribution with a small height. For wide target distributions, i.e., Da/α>>1, decreasing of Da/α is desirable to decrease capture time. Therefore, for these cases, it is desirable to concentrate the target into a narrow distribution, such as by ITP. Since ITP has been demonstrated to increase target concentration up to $10^6$ fold (Jung et al. (2006) Anal. Chem. 78: 2319-2327), our technique can potentially speed up AC by as much as $10^6$ fold compared to traditional AC.

Furthermore, in the Da/α>>1 regime preconcentrating with ITP improves column utilization for a set assay time. Assay time is set by the time needed to advect the target into the affinity region, which scales as σ/u. Therefore for a given assay time, σ/u is fixed. If the operator desires to capture approximately 95% of the target, the assay time should be around $p_t$. This condition thus fixes Da/α for a given affinity column and application buffer, i.e., a fixed $k_1 N$. Preconcentrating with ITP decreases the target distribution width a, therefore for this case reducing the application velocity u. Since the column is operated at reduced application velocity, the penetration depth $p_z$ is also reduced (see Section 2.3). Hence, preconcentrating with ITP can improve column utilization.

2.5 Control of Capture Efficiency

Figure 5B:
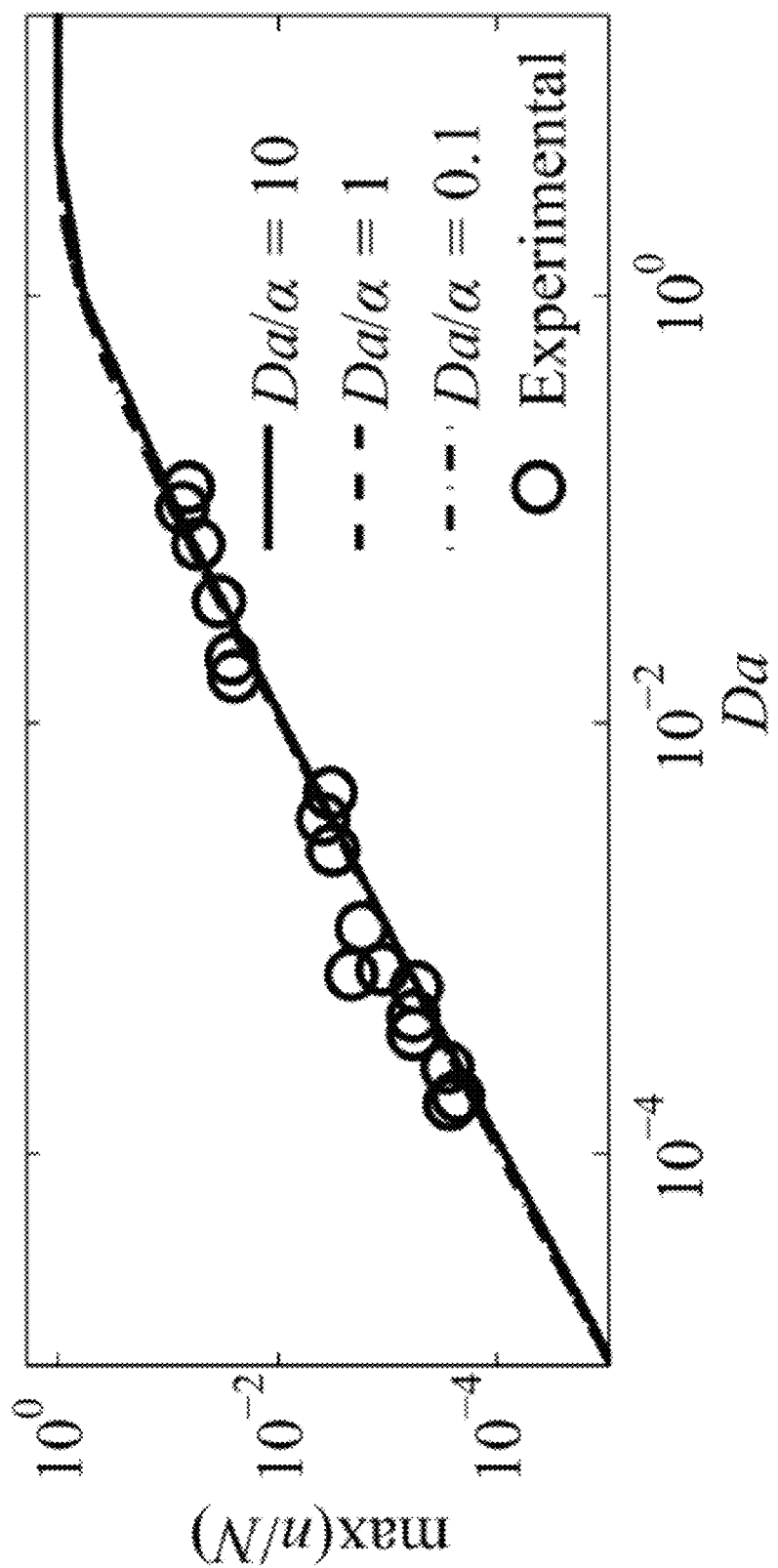

We define the capture efficiency as the concentration of target captured over the initial concentration of probe. For small values of β, n/N increases linearly with Da until a Da of unity (FIG. 5B). For Da≥1, the affinity region becomes locally saturated at n/N=1. Similarly, for a particular scaled target distribution width Da/α, N/n increases linearly with α for less than the critical α (where the affinity region is not saturated). For α larger than the critical α, the affinity region becomes locally saturated and n/N=1.

2.3.3 Effect of Non-Dimensionalized Equilibrium Dissociation Constant

Figure 3A:
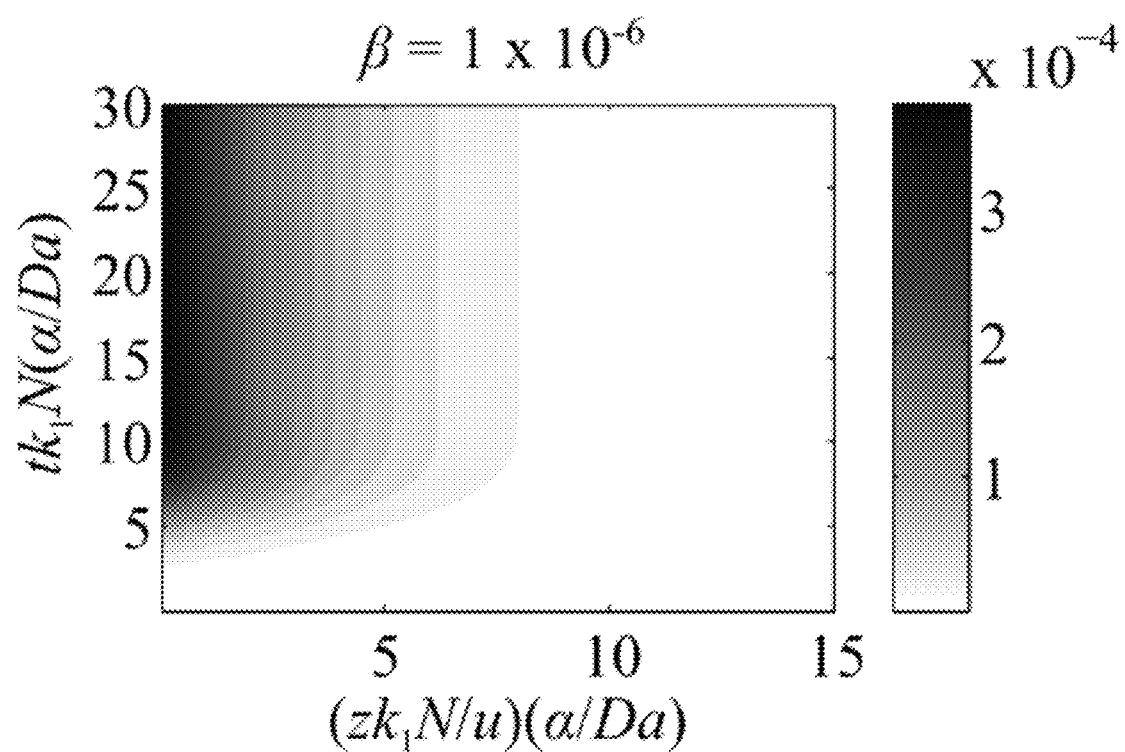
FIGS. 3A-3D show model predictions of the effect of non-dimensionalized equilibrium dissociation constant β on the capture dynamics of ITP-aided affinity capture into a semi-infinite affinity region.
Figure 3B:
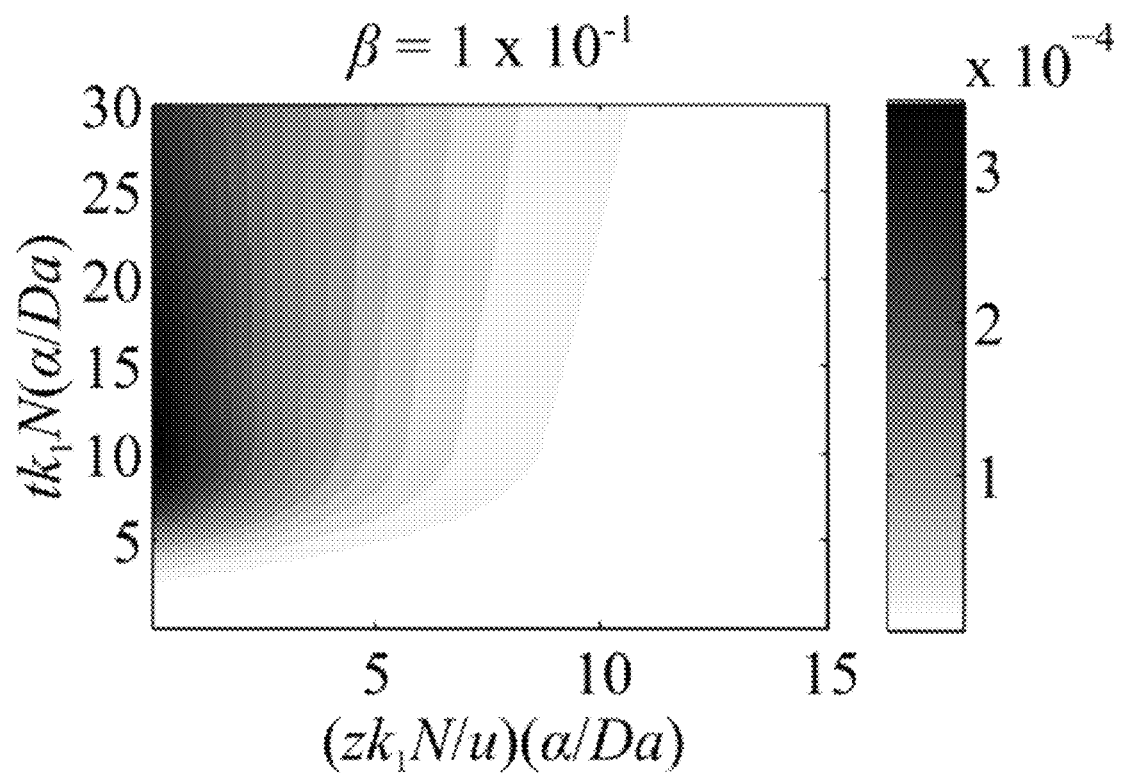
Figure 3C:
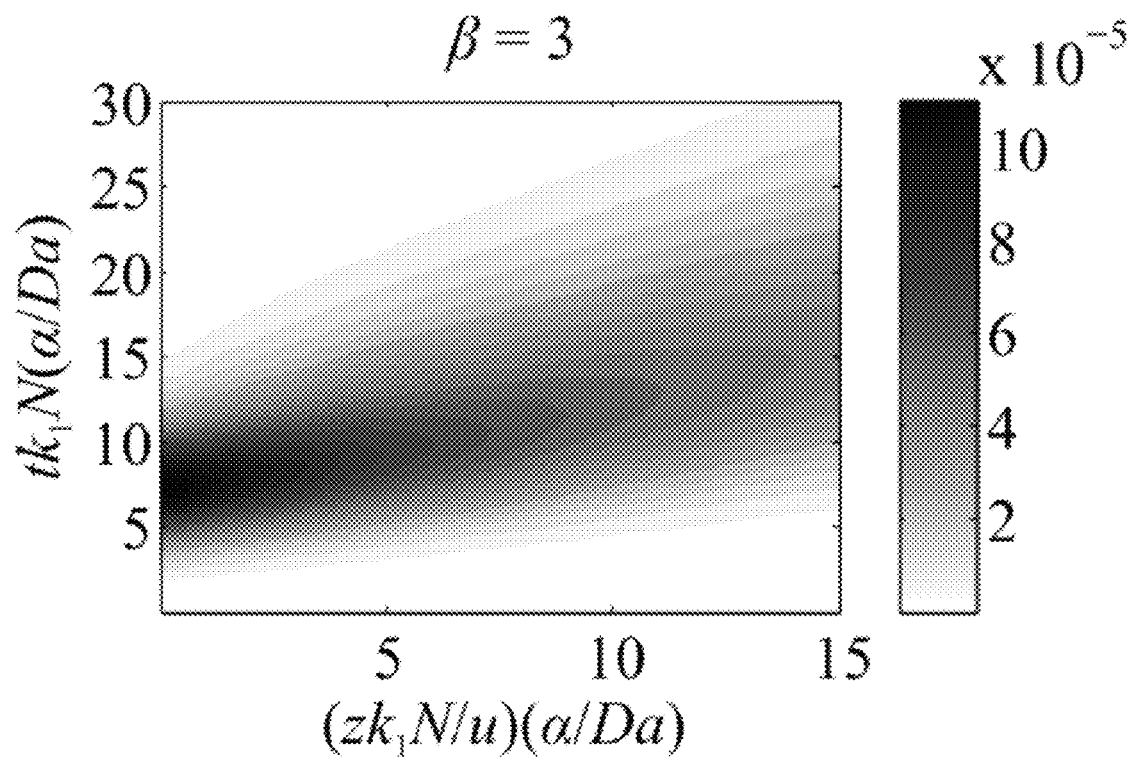

The parameter β describes the relative importance of the forward (capture reaction) to the reverse (dissociation reaction). Until now, we have concentrated on the regime of low β, where the effects of dissociation are negligible and the reaction appears irreversible. As β increases, target-probe binding becomes a reversible process. Therefore the target unbinds on timescales close to the advection time scale and so the target penetrates deeper into the affinity region. We summarize these trends in FIG. 3. In FIGS. 3A, 3B, and 3C we plot the concentration of bound target scaled by probe density, n/N, for Da=4.3×$10^{-4}$, α=1.1×$10^{-3}$, and β from $10^{-6}$ to 3. In these spatiotemporal plots we plot the cross-sectional area-averaged n/N in the affinity region versus scaled distance along the axis of the channel, and scaled time. Da=4.3×$10^{-4}$, α=1.1×$10^{-3}$ are parameter values for a typical ITP-AC experiment and were in fact those used for the experiment which we show in FIG. 4E. For this set of Da and α, when β is relatively low ($10^{-6}$) the target only penetrates approximately 3 advection-reaction length scales into the affinity region (FIG. 3A). As β increases (e.g., β=$10^{-1}$), the target begins to penetrate deeper into the affinity region (FIG. 3B). As β increases further, the definition of capture length, i.e. the length needed to capture 95% of the target irreversibly (as defined above) becomes invalid, as the target migrates through the affinity region instead of being captured. For this set of Da and α, this is very prominent at β=3 (FIG. 3C).

Figure 3D:
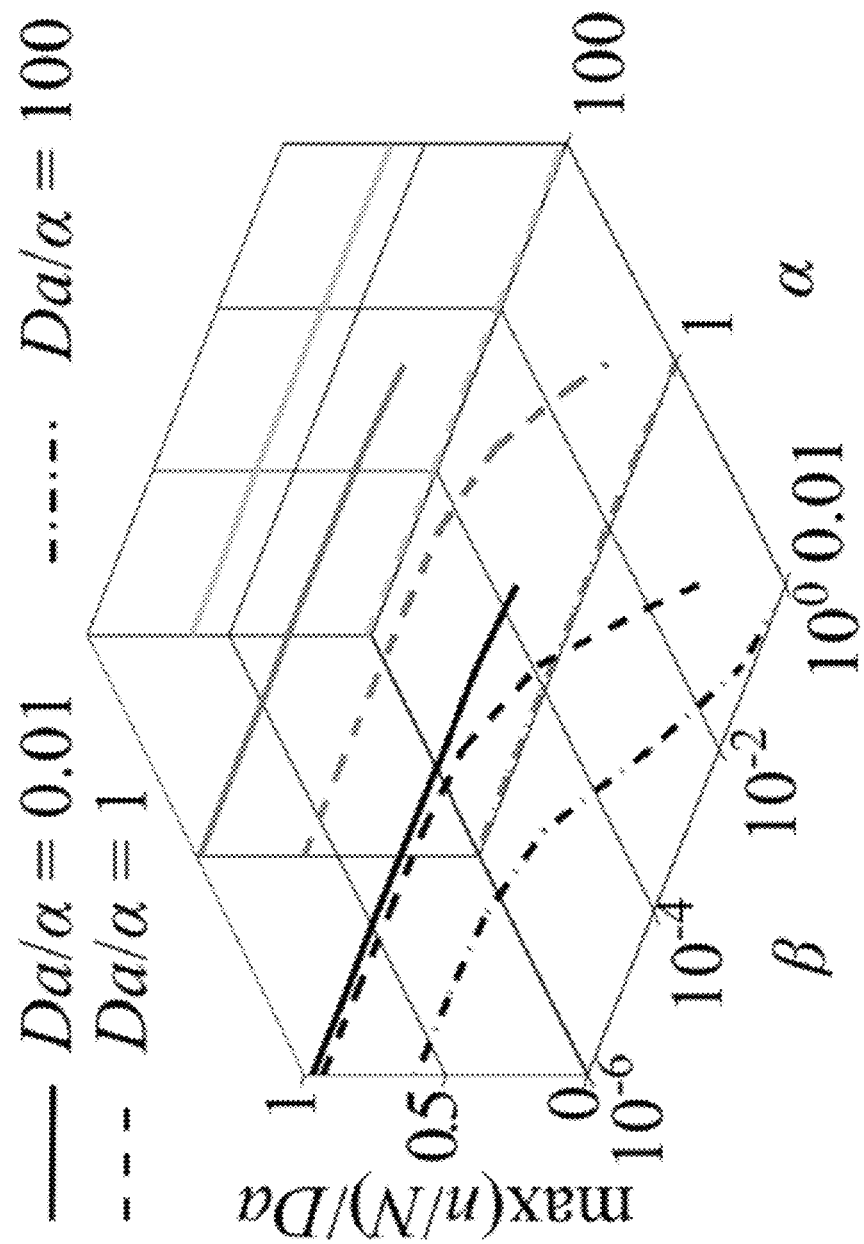

In FIG. 3D, we summarize the effect of β on capture efficiency as a function of both Da and a, and we plot max(n/N) scaled by Da. Overall, as β increases, the capture efficiency decreases as the capture and dissociation of the target "smears" it over a larger area of the affinity region (FIG. 3D). As the affinity region becomes more locally overloaded (α approaches and becomes greater than 1), the effect of decreasing capture efficiency with increasing β becomes more pronounced. On the other hand, at smaller Da/α (smaller peak widths), for the same effective loading, the decrease of capture efficiency with increasing β is less pronounced. This suggests that operating with smaller Da/a (such as with strong ITP preconcentration) allows capture of targets with higher dissociation constants.

3. Experimental

We here describe materials, discuss the choice of chemistry, the fabrication and DNA functionalization of the PPM, our ITP-AC protocol, and our choice of ITP-AC buffer chemistry.

2014. 3.1 Materials and Instrumentation

Ethylene dimethacrylate (EDMA-CAS #97-90-5), glycidyl methacrylate (GMA-CAS #106-91-2), inhibitor removal media (product number: 311332-CAS #9003-70-7), azobisisobutyronitrile (CAS #78-67-1), 3-(trimethoxysilyl) propyl methacrylate (TSPM-CAS #2530-85-0), sodium dodecyl sulfate (SDS), acetone, and methanol (MeOH) 99.93% were purchased from Sigma Aldrich. n-hexane HPLC grade 95+% was purchased from Alfa Aesar. Saline-sodium citrate (SSC) buffer 20× was from Invitrogen (Carlsbad, Calif.). Fish sperm DNA (CAS #100403-24-5) was from Amresco (Solon, Ohio). Synthetic oligos were purchased from Integrated DNA Technologies (Coralville, Iowa).

We performed ITP-aided affinity chromatography experiments in VWR 53432-728 micropipet capillaries (inner diameter 501 μm, borosilicate glass) (Visalia, Calif.) secured in a custom built capillary set up, which interfaced LE and TE reservoirs to capillary (see SI Section SI7). We performed experiments in galvanostatic mode with a Keithley 2410 high voltage sourcemeter (Keithley Instruments, Cleveland, Ohio).

We monitored our experiments and performed fluorescence measurements of the PPM with an Olympus IX70 inverted fluorescence microscope equipped with 4× (NA of 0.16) and 2× (NA of 0.08) objectives (Olympus, Hauppauge, N.Y.), a model XF110-2 and XF115-2 filter cubes (Omega Optical, Brattleboro, Vt.), and 627 nm red and 470 nm blue LEDs (ThorLabs Newton, N.J.) for illumination. We captured images with a 12-bit, 2048×2048 pixel charge coupled device (CCD) camera with 7.4×7.4 μm pixels (Photometrics CoolSNAP K4) controlled with WinView software, (Roper Scientific, Trenton, N.J.). We post-processed the images with custom in-house scripts written in MATLAB (Mathworks, Natick, Mass.).

3.2 Polymer Chemistry

Affinity chromatography columns require surfaces to which affinity ligands can be readily bound, but which provide minimal non-specific binding. Reproducible and robust affinity chromatography experiments with aqueous solutions also benefit from sufficiently hydrophilic surfaces. We therefore chose a polymerization chemistry that incorporates the monovinyl monomer, GMA, which has an epoxide functional group, which we crosslinked with EDMA. The epoxide group on GMA is well known to be highly reactive to primary amines on biopolymers such as nucleic acids (Schwarzenbach et al. (2011) Nat. Rev. Cancer 11:426-437; West et al. Microchip-Based Assay Systems, Springer, 2007, p. 9) and proteins (Ma et al. (2007) J. Sep. Sci. 30:3050-3059; Sinitsyna et al. (2012) Talanta 93:139-146; Krenkova et al. (2005) J. Sep. Sci. 28:1675-1684) and other well-known affinity ligands (Mallik et al. (2006) J. Sep. Sci. 29:1686-1704). Furthermore, GMA-EDMA polymers exhibit little non-specific binding with nucleic acids and are non-sieving. GMA-EDMA polymers also possess sufficiently hydrophilic surfaces for facile introduction of aqueous solutions into the porous polymer. Lastly, methacrylate PPM are highly scalable and have been synthesized in both microfluidic and 8 L scale formats (Rohr et al. (2001) Electrophoresis 22:3959-3967; Yu et al. (2002) Journal of Polymer Science: Part A Polymer Chemistry 40:755-769; Yu et al. (2000) Electrophoresis 21:120-127; Yu et al. (2001) Anal. Chem. 73:5088-5096; Podgornik et al. (2004) J. Biochem. Bioph. Methods 60:179-189).

We cross-linked GMA with EDMA via a free radical, UV-initiated polymerization in the presence of MeOH and hexane as solvents, with AIBN as photoinitator (Shkolnikov et al. (2010) Sens. Actuator B-Chem. 150:556-563). We chose photo, rather than thermal, initiation for the present polymerization to be able to lithographically define regions of PPM. Ability to lithographically define PPM regions is valuable for incorporation of PPM in microfluidic chips for, for example, multiplexed affinity purification.

3.2 Polymethacrylate Porous Polymer Monolith (PPM) Synthesis

Both EDMA and GMA were received with polymerization inhibitors, which we removed by passing through columns packed with inhibitor removing media. We then mixed the photo initiator AIBN (10 mM), GMA (8% v/v), EDMA (12% v/v), MeOH (16% v/v) and hexane (64% v/v) in a polypropolyne vial. We injected a slug of this polymerization solution in a previously prepared, dry, micropipet capillaries with vinylized walls.

We vinylized the walls of the capillaries by placing the capillaries in a solution of 30% (v/v) TSPM, 70% (v/v) acetone solution overnight and then flushing the remaining solution with air (Yu et al. (2001) Anal. Chem. 73: 5088-5096). The capillary walls were vinylized to ensure covalent attachment of the polymer to the capillary wall, and thus avoid channeling (Yu et al. (2001), supra). We then irradiated samples using a 12 W, approximately 365 nm peak wavelength UV lamp (Chauvet, Sunrise, Fla.), at 12 cm exposure distance, for 2 hours. After polymerization, we flushed the samples with air to remove unreacted monomers and solvents, and dried at 20° C. under ~93 kPa vacuum for 30 minutes. This resulted in 1 to 3 cm long GMAEDMA PPM structures bound to the capillary wall with ~80% (measured) void fraction and order 2 μm pores (see FIG. 1B and SI Section SI6). This ensured that the porous affinity region had small hydrodynamic resistance, facilitating filling the system with LE buffer, and later the elution buffer without the need for high pressure pumps.

3.3 Probe DNA Immobilization on PPM

We prepared DNA immobilization solution consisting of 3×SSC buffer (450 mM sodium chloride, 45 mM trisodium citrate), 20 mM SDS and 250 μM 5' amine modified synthetic oligo DNA (West et al. Microchip-Based Assay Systems, Springer, 2007, p. 9). We slowly injected a slug of this immobilization solution into the micropipet capillaries with the PPM inside. We then placed micropipet capillaries in a water bath at 70° C. for 2 hours. Subsequently we flushed each capillary with 2 ml of DI water (~500 column volumes) and then dried at 70° C. under about 93 kPa gauge vacuum for 1 hour.

We measured the resulting volumetric density of immobilized DNA by immobilizing 5' amine, 3' Cy5 modified synthetic oligo DNA and measuring the resulting fluorescence intensity of the PPM. To obtain the volumetric density of immobilized DNA, we compared the fluorescence intensity of the PPM to a calibration of fluorescence intensity versus Cy5 labeled DNA concentration (see SI, Section SI4).

We measured the volumetric density of immobilized DNA to be about 30 µM. For a rough estimate of surface density of immobilized DNA, we roughly approximate the PPM as consisting of a simple closed-packed cubic spheres with 1 µm diameter (see FIG. 1B). This provides an estimate of immobilized DNA surface density of $1.2 \times 10^{-12}$ molecules $cm^{-2}$. DNA probe surface densities of around $2 \times 10^{-12}$ molecules $cm^{-2}$ have been shown to provide high (>60%) hybridization efficiencies, while at higher probe surface densities, hybridization efficiencies decrease (Peterson et al. (2001) Nucleic Acids Res. 29:5163-5168). Peterson et al. attribute this to repulsive electrostatic and steric interactions that increase with increased probe density (Peterson et al., supra). We therefore expected both a high column utilization (due to high probe density) and high hybridization efficiency for our PPM.

3.4 ITP-Aided Affinity Chromatography Protocol

We performed ITP-AC experiments in a custom built capillary setup, which interfaced LE and TE reservoirs to the capillary with the PPM (SI Section SI7). The capillary had 1 to 3 cm long GMA-EDMA PPM structures polymerized inside of it, and the PPM was attached to the capillary wall. The surface of GMA-EDMA PPM was functionalized with 25 nucleotide DNA probe complimentary to the target. We began ITP-AC by filling the LE reservoir and the capillary with the affinity column with the LE buffer by applying about 68 kPa vacuum to the TE reservoir. We then mixed the sample containing the target with the TE buffer and placed this in the TE reservoir (FIG. 1A, Step 1). We then applied a constant current, inducing ITP. The LE ions in the capillary migrated toward the LE reservoir followed by the TE ions. The target ions (DNA) had intermediate electrophoretic mobility between LE and TE ions and therefore overspeed the TE ions and concentrated (~100-fold) at the LE-TE interface into a sharp, Gaussian-like peak (FIG. 1A, Step 2). The target DNA was labeled and visualized with fluorescent Cy5 dye. For unlabeled DNA the spatiotemporal behavior of the LE-TE interface can be non-invasively monitored, for example, with species altered fluorescence imaging (Shkolnikov et al. (2013) Lab Chip 13:1632-1643). Any matrix ions with electrophoretic mobilities lower than that of the TE were separated from the target (FIG. 1A, Step 2). The concentrated target then migrated into the porous affinity region and was captured by the immobilized probe there (FIG. 1A, Step 2; FIG. 1B). The LE-TE interface continued to migrate through the affinity region and beyond. After the LE-TE interface migrated far enough from the capture region, we then removed the LE and TE buffers with vacuum. We then eluted the captured target (FIG. 1A, Step 4) with an elution buffer, 50 mM NaOH, which we quenched with 200 mM HEPES right after elution.

3.5 ITP-AC Choice of Buffer Chemistry

In all our experiments the LE buffer consisted of 250 mM HCl and 500 mM Tris. The TE buffer as placed in the TE well consisted 25 mM HEPES, 50 mM Tris and some amount of target and/or contaminating species. The LE ion (here chloride) maintains its concentration thought the experiment and sets the adjusted TE ion (here HEPES) concentration, i.e., the TE ion concentration behind the LE-TE interface (Everaerts et al. Isotachophoresis: Theory, Instrumentation, and Applications, Elsevier, Amsterdam, New York, 1976; Bocek, Analytical Isotachophoresis, VCH, Cambridge, 1987). The TE ion concentration can be calculated based on the LE ion concentration using a jump condition across the LE-TE interface such as the Kohlrausch condition or Albery-Jovin condition (Hruska et al. (2007) Electrophoresis 28:3-14). The adjusted TE ion concentration is generally 0.5-0.8 that of the LE ion (Hruska et al., supra). In our experiments the adjusted TE concentration was calculated to be 150 mM using an electrokinetic simulation software SPRESSO (Bercovici et al. (2009) J. Chromatogr. A 1216:1008-1018).

We chose a relatively high LE concentration (and therefore high adjusted TE concentration) to ensure that the application buffer, formed by the overlap of the LE and TE, is of high ionic strength. This was done to suppress the double layers both on the surface of the PPM and around the nucleic acids (Kirby et al. (2004) Electrophoresis 25:187-202). This decreases electrostatic repulsion between the target DNA and probe DNA thus increasing DNA hybridization (Peterson et al. (2001) Nucleic Acids Res. 29: 5163-5168; Springer et al. (2010) Nucleic Acids Res. 38:7343-7351). This, together with large PPM pore size, also leads to low surface charge to bulk charge ratio in the PPM. This minimizes the effects of concentration polarization (Mani et al. (2009) Langmuir 25:3898-3908; Zangle et al. (2009) Langmuir 25:3909-3916) and Donnan exclusion (Waki et al. (1982) J. Liq. Chromatogr. 5:105-119; Waki et al. (1980) J. Chromatogr. A 201:259-264), which could have otherwise excluded the target from the affinity capture region. The high ionic strength of the TE and LE was also chosen to suppress EOF (Kirby et al. (2004) Electrophoresis 25:187-202; Kirby et al. (2004) Electrophoresis 25:203-213).

We chose chloride as the LE ion as it is relatively fast (fastest commonly encountered anion) (Hirokawa et al. (1983) J. Chromatogr. A 271:D1-D106) and has higher electrophoretic mobility then nucleic acids (Stellwagen et al. (1997) Biopolymers 42:687-703). Chloride is also present in many biological samples (e.g., blood, urine, intra and extracellular fluids) in significant amounts (Costanzo Physiology, Saunders, 2009). For example, if we chose a LE ion that was slower than chloride (but faster than nucleic acids) and mixed a chloride rich biological sample with the TE, chloride would have overspeed through that LE. Overspeeding through the LE would have disrupted ITP and thus the concentration of target at the LE-TE interface, which is necessary for ITP-AC. Therefore choosing chloride as the LE ion enabled our assay to be compatible with many biological samples. We chose HEPES as the TE ion because while its mobility is low enough (in the presence of Tris as the counterion) to focus DNA, it is high enough to exclude many matrix ions (e.g. PCR inhibitors found in blood) (Hirokawa et al., supra; Stellwagen et al., supra; Wilson et al., supra; Persat et al. (2009) Anal. Chem. 81:9507-9511). We chose Tris as a counterion to provide a pH of about 8.2 for the application buffer (Hirokawa et al., supra), and thus provide an amenable environment for hybridization (Edman et al. (1997) Nucleic Acids Res. 25:4907-4914).

4. Results and Discussion

To validate our model we performed ITP-AC experiments with 25 nucleotide DNA Cy5-labeled target and 25 nucleotide DNA probe immobilized onto a polymethacrylate porous polymer monolith. In these experiments we measured the target migration in ITP and its subsequent hybridization reaction with the immobilized probe. In our experiments we varied Da over 4 orders of magnitude by varying target amount and ITP velocity. We compared both the measured spatiotemporal behavior of ITP-AC and key AC parameters such capture length and capture efficiency to those predicted by our model. Lastly, we demonstrated purification of 25 nucleotide DNA target from 10,000-fold more abundant contaminating fish sperm DNA.

4.1 Spatiotemporal Behavior of ITP-AC

We observed and quantified the spatiotemporal behavior of ITP-AC by tracking the target while it was migrating in ITP in free solution and while it was reacting with the immobilized probe in PPM. In FIGS. 1B, 4D, 4E, and 4F we showed the Cy5 labeled-target DNA reacting with the immobilized probe. We plotted the cross sectional area averaged Cy5 fluorescence intensity in the PPM versus distance along the axial coordinate and time.

For experiments shown in FIGS. 4D, 4E, and 4F we spiked 10 nM, 100 pM, and 100 pM target DNA into the TE respectively. We then performed ITP in galvanostatic mode (as described in Section 3.4) with capture currents of 200 µA, 200 µA, and 600 µA respectively. For experiment shown in FIG. 1B we spiked 10 nM target DNA into the TE and also performed ITP in galvanostatic mode with capture currents of 200 µA. Both the ITP velocity and the electroosmotic flow velocity are proportional to current. For this system, the electroosmotic flow is in the direction opposite of the LE-TE interface migration, and therefore decreases the ITP velocity. The electric field at the LE-TE interface is also proportional the current in the system. This electric field counteracts target dispersion and therefore target distribution width is inversely proportional the current in the system (Garcia-Schwarz et al. (2011), supra; MacInnes et al. (1932) Chem. Rev. 9:171-230; Shkolnikov et al. (2012) Phys. Chem. Chem. Phys. 14(32):11534-11545; Bhattacharyya et al. (2013) Phys. Fluids 25:022001). Therefore the current in the system simultaneously controlled the net target velocity and the target distribution width.

For experiments shown in FIGS. 4D, 4E, and 4F, as well as those in FIG. 5, $Da/\alpha$ was on the order of 1, and the ITP preconcentration was about 100-fold. We did not preconcentrate further, because doing so would not significantly decrease $p_t^*$ and therefore would not improve assay time and/or column utilization (see Section 2.4 and FIG. 2B).

In FIGS. 4A, 4B, and 4C we showed the spatiotemporal behavior of affinity capture with ITP predicted by our model for experimental conditions of 4D and 4F, respectively. To obtain the appropriate values for model parameters ($\alpha$, $\beta$, $Da$) from experimental data, we measured u, $\alpha$, n and N, predicted $K_d$, and fitted $k_1$ to the model based on 18 independent experiments. We obtained a $k_1$ of $1.5 \times 10^3$ $M^{-1}$ $s^{-1}$ which is consistent with that observed by Gao et al. for surface hybridization of DNA with some secondary structure (Gao et al. (2006) Nucleic Acids Res. 34:3370-3377). For example, Gao et al. obtained forward rate constants from $3 \times 10^3$ $M^{-1}$ $s^{-1}$ for probe and target with some secondary structure to $5 \times 10^4$ $M^{-1}$ $s^{-1}$ for probes and target with little secondary structure for 25 nucleotide probes and targets (Gao et al., supra). For calculated secondary structure of our target and probe see SI Section SI5. We measured u directly from spatiotemporal data of target migration in free solution in front of the PPM. We measured $\alpha$ and n by measuring fluorescence intensity in the spatiotemporal fluorescence data and by interpolating on a Cy5 fluorescence versus DNA concentration calibration curve (SI, Section SI5). Similarly, in separate experiments, we measured N by measuring fluorescence intensity of Cy5 modified probe bound to the PPM and interpolating on a Cy5 fluorescence—DNA concentration curve. We calculated $K_d$ from predicted two-state melting (hybridization) $\Delta G$ from mFold (State University of New York at Albany) using the Van't Hoff equation (see SI, Section S14) For all our experiments, $K_d$ was $\sim 3 \times 10^{-22}$ M and $\beta$ was $1 \times 10^{-17}$, far lower than a $\beta$ for which any decrease of capture efficiency or streaking could be expected from target dissociation from the affinity probe. We obtained $p_z$ by integrating the fluorescence intensity with respect to the axial coordinate and finding the distance from the PPM start where the integrated intensity was 95% of the total integrated intensity.

To obtain the spatiotemporal plot from the model we neglected the effects of photobleaching and assumed a proportional relationship between the fluorescent intensity of Cy5 and target concentration. The model predicts that upon reaching the monolith target begins to bind immediately with the affinity probe, penetrating only about 2.8 advection-reaction length scales into the affinity region. Upon binding a steady state is reached and the target persists on the PPM.

As we show in FIG. 1B, the target focused in ITP migrated at constant velocity in a Gaussian like distribution toward the PPM. This supports the modeling assumption that the ITP focuses the target into a Gaussian like profile (which suggests the boundary condition in equation (4)). Upon reaching the monolith, as we show in FIG. 1B and FIGS. 4D, 4E, and 4F, the target began to bind immediately with the affinity probe, penetrating only about 2.8 advection-reaction length scales into the affinity region. As shown in FIG. 1B, there is a slight increase in fluorescence intensity (~1.7×) when the target enters the PPM. This effect was observed both with ITP and without ITP in a PPM without immobilized probes (see Section SI4 of SI). We attributed this to the optical properties of the PPM and corrected for this when measuring $\alpha$, n and N.

In the experiments shown in FIG. 4D, the target concentration was larger than that in 4E, and 4F, therefore the captured target fluorescence intensity (proportional to n/N) was larger than that in 4E, and 4F. In experiments shown in FIG. 4F the system current was larger than that in 4D, and 4E, therefore causing a larger target velocity and deeper penetration into the PPM then in experiments shown in 4D, and 4E. For all three experiments, upon penetrating approximately 2.8 advection-reaction length scales into the affinity region a steady state was reached and the target persisted on the PPM as expected.

The spatiotemporal distribution of target for both experiments in FIGS. 4B and 4D agree very well with that predicted by our model. For the experiment shown in FIG. 4D, $p_z$=0.93 mm and max (n/N)=$7.2 \times 10^{-2}$; for the corresponding theoretical prediction shown in FIG. 4A, $p_z$=1.03 mm and max (n/N)=$8.3 \times 10^{-2}$, which is within 11%, and 15%, respectively of experimentally measured values. The predicted spatiotemporal behavior of ITP-AC also qualitatively agreed very well with that experimentally observed. We attribute the small "tails" in FIG. 4D, to small amounts impurity present with the target that did not get captured by the affinity region. For the experiment shown in FIG. 4E, $p_z$=0.91 mm and max (n/N)=$5.8 \times 10^{-4}$; for the corresponding theoretical prediction in FIG. 4B, $p_z$=0.97 mm, and max (n/N)=$3.9 \times 10^{-4}$, which is within 7%, and 33% respectively of experimentally measured values. The predicted spatiotemporal behavior of ITP-AC again also qualitatively agreed very well with that experimentally observed. We again attribute the small "tails" in FIG. 4F to small amounts of impurities present with the target that did not get captured by the affinity region.

For the experiment in FIG. 4F, the $p_z$=2.8 mm and max (n/N)=$2.7 \times 10^{-4}$; for the corresponding theoretical prediction in FIG. 4C, $p_z$=2.5 mm and max (n/N)=$1.6 \times 10^{-4}$, which is within 11%, and 41% respectively of experimentally measured values. The predicted spatiotemporal behavior of ITP-AC also qualitatively agreed fairly well with that experimentally observed. We attributed the difference in slope of the fluorescence as the target began binding to the PPM between the theory in FIG. 4C and experiment in 4A to the assumption of continuously constant velocity in our model (see equation (1)). In our model, shown in FIG. 4, the target velocity is constant, and therefore the slope of fluorescence is also constant. In the experiment, as the target was entering the PPM, the target slowed down (possibly due to interactions with the immobilized probes) which reflects the fluorescence slope in FIG. 4F. Despite this, there is good agreement between the theory and experiment for the penetration depth.

Overall, our model qualitatively showed good agreement with experiments for over 3 orders of magnitude of target concentration. We attributed other slight discrepancies between theoretical predictions (FIGS. 4A, 4B, and 4C) and experimental observations (FIGS. 4D, 4E, and 4F) to small inhomogeneities in the PPM resulting in slightly non-homogeneous immobilized probe distribution. We hypothesized that this inhomogeneity was caused by air trapped in the pores, which was trapped with a slightly different, random, distribution for each experiment. This trapped air blocked access to the immobilized probes causing effective inhomogeneity in probe distribution. This hypothesis is supported by our observations that the PPM material was somewhat hydrophilic, and thus trapped the less wetting phase (air) inside the pores.

4.2 Effect of Da on Scaled Capture Length

To validate our theoretical predictions for scaled capture length $p_z^*$, we measured $p_z^*$ for 18 ITP-AC experiments varying Da from $10^{-4}$ to $10^{-1}$. We varied Da by varying both the target concentration in the TE well (100 pM to 10 nM) and capture current (200 µA to 600 µA). We kept Da<1 in our experiments, as to not locally saturate the affinity capture region. We again performed these experiments in galvanostatic mode, as described in Section 3.4.

To obtain $p_z^*$, we obtained $p_z$ and u from the spatiotemporal data and N from a separate experiment, and $k_1$ by fitting to the model (assuming $p_z^*$ for all experiments ~2.8) (see section 4.1). We obtained $p_z$ by integrating the fluorescence intensity with respect to the axial coordinate and finding the distance from the PPM start where the integrated intensity was 95% of the total integrated intensity. We plotted the measured $p_z^*$ and the theoretically predicted $p_z^*$ as a function of Da in FIG. 5A.

We observed that over 4 orders of magnitude from $10^{-4}$ to $10^{-1}$, the measured $p_z^*$ varied only by 18% (standard deviation/mean). The variation appeared to be non-systematic (FIG. 5A). Therefore theoretical prediction that $p_z^*$ is constant in this range of Da agreed well with experimental observations. We again attributed the small discrepancy in $p_z^*$ from experiment to experiment to the inhomogeneity in the PPM, due to trapping of air in the PPM, leading to an inhomogeneity in the probe distribution (see Section 4.1).

4.3 Effect of Da on Capture Efficiency

To validate our theoretical predictions for maximum capture efficiency max(n/N) we measured max(n/N) for 18 ITP-AC experiments varying Da from $10^{-4}$ to $10^{-1}$, same as in section 4.2. We again kept Da<1 in our experiments as to not locally saturate the affinity capture region. As Peterson et al. showed, saturating an affinity region with high probe density of DNA is not always experimentally possible due to electrostatic repulsion of DNA (Peterson et al., supra).

To obtain max(n/N) we measured max(n) from the spatiotemporal data and N from a separate experiment (see Section 3.3). We obtained max(n) by measuring the maximum fluorescence intensity of a bound target after a steady state was reached (i.e. the distribution of target was not changing). We then obtained max(n) by interpolating the fluorescence intensity on a Cy5 fluorescence intensity versus DNA concentration calibration curve (SI, Section SI4). We plot the measured max(n/N) and the theoretically predicted max(n/N) as a function of Da in FIG. 5B.

We observed that over 4 orders of magnitude from $10^{-4}$ to $10^{-1}$ the measured max(n/N) increased linearly with Da and this agreed very well with the theoretically predicted variation in max(n/N) with Da. We attribute the random variation in max(n/N) to the experiment-to-experiment variation in inhomogeneity of N due to trapping of air in the PPM (as discussed in Section 4.1).

4.4 Sequence Specific Extraction of Target from $10^4\times$ More Abundant Contaminant Finally, as a demonstration of ITP-AC we separated the Cy5 labeled 25 nucleotide oligo DNA from 10,000 fold more abundant genomic fish sperm DNA. For this experiment we placed 0.1 µg ml$^{-1}$ Cy5 labeled target (total 0.02 µg) and 1000 µg ml$^{-1}$ fish sperm DNA (total 200 µg), visualized by 0.1×SYBR Green I, into the TE well. We then performed ITP in galvanostatic mode (as described in Section 3.3) with capture current of 200 µA. We visualized this experiment independently in the SYBR Green I channel (visualizing only the fish sperm DNA) and in the Cy5 channel (visualizing only the target).

Figure 6A:
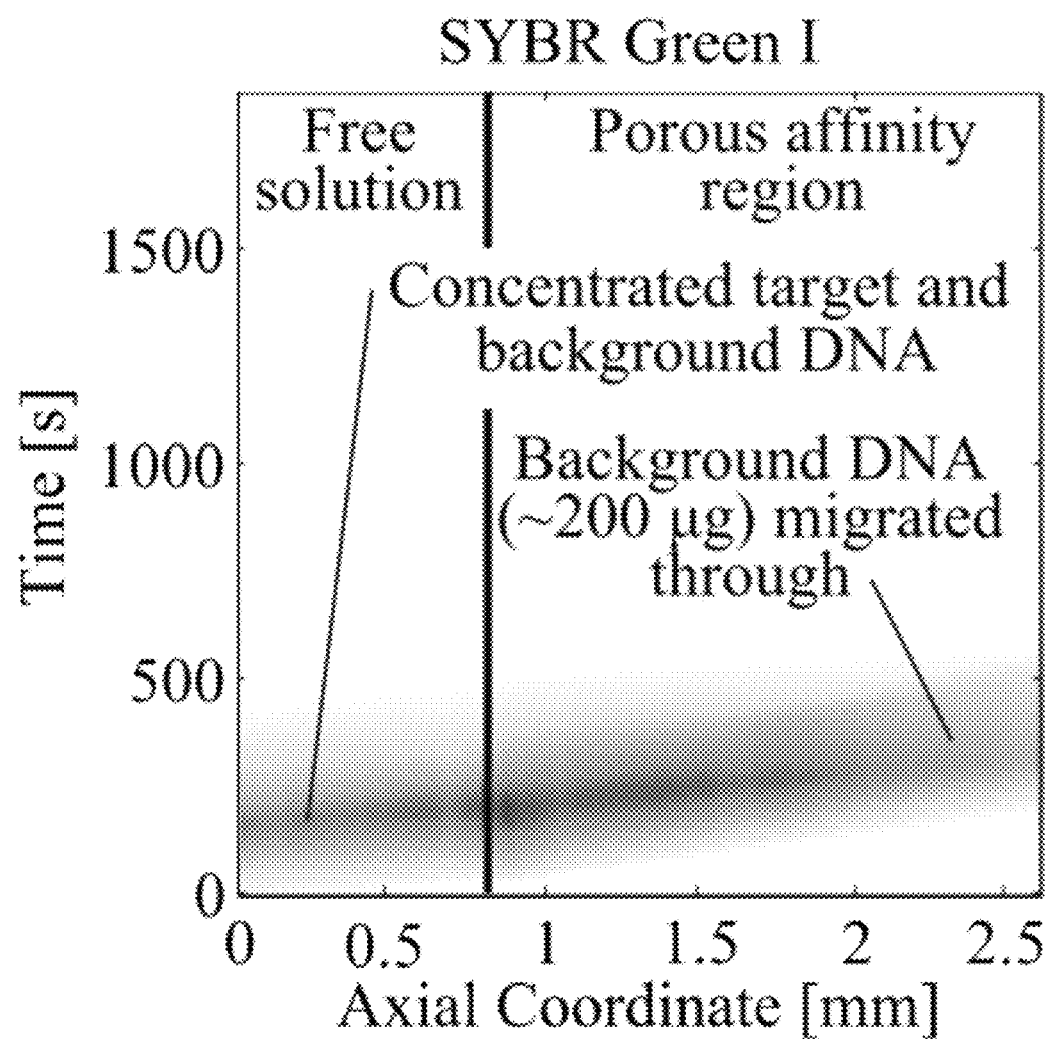
FIGS. 6A-6C show spatiotemporal plots showing separation of rare target DNA from 10,000-fold more abundant contaminating DNA using ITP-AC.

In FIG. 6A we show the spatiotemporal plot of observed fluorescence from the experiment in the SYBR Green I channel. The fish sperm DNA migrated in ITP from free solution into the PPM and continued to migrate in ITP. It was not captured by the immobilized probe on the PPM. We attribute the observed slight decrease in migration velocity of ITP in the PPM due to higher electroosmotic flow in the PPM. We hypothesize that the increased EOF was due to higher charge of the PPM (in comparison to the glass walls of the capillary) which was due to the immobilized probe DNA. EOF from a negatively charged surface would be in the direction opposite to the LE-TE interface migration direction, and hence slow the LE-TE interface, as was observed. Furthermore, since fish sperm DNA was not captured by the PPM, we conclude that there is little non-specific binding of DNA to GMA-EDMA PPM.

Figure 6B:
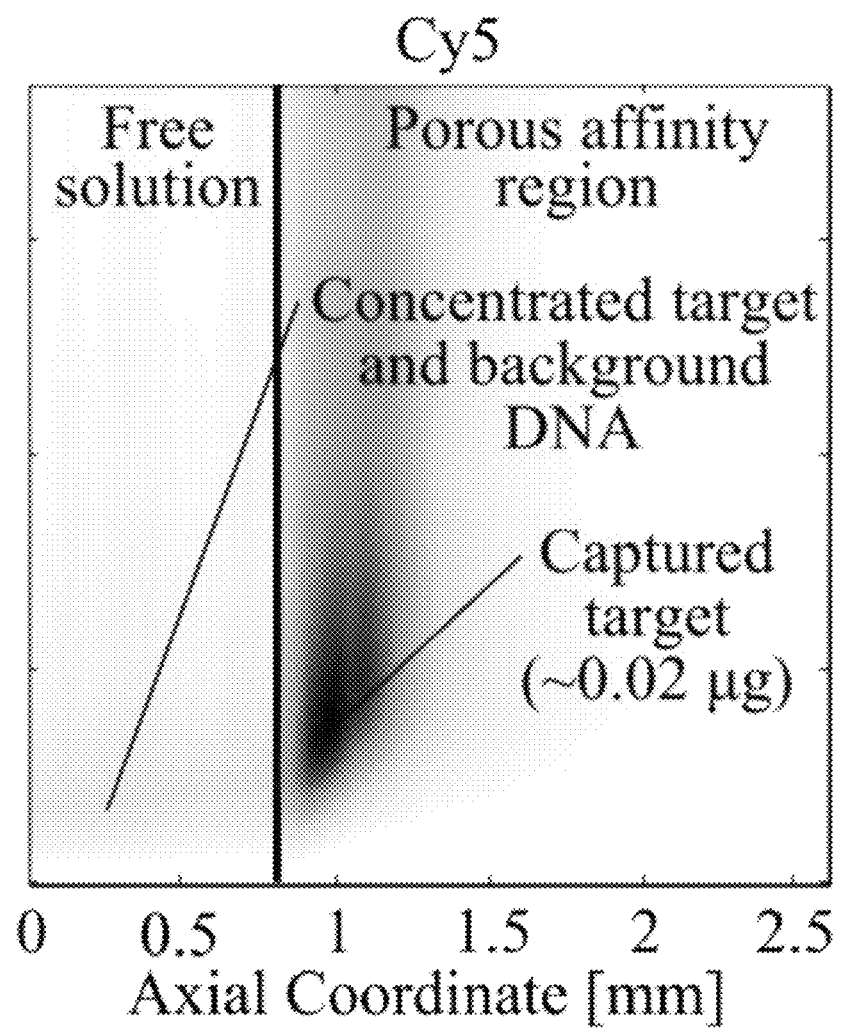

In FIG. 6B we show the spatiotemporal plot of observed fluorescence from the experiment in the Cy5 channel. The target DNA migrated in ITP from free solution into the PPM and immediately became captured by the immobilized probe on the PPM. The presence of 10 000 fold more abundant contaminating DNA did not interfere with the capture of the target. We attribute the decrease in Cy5 fluorescence over time (which becomes prominent in FIG. 6B after 1000 seconds) to photobleaching of Cy5.

Figure 6C:
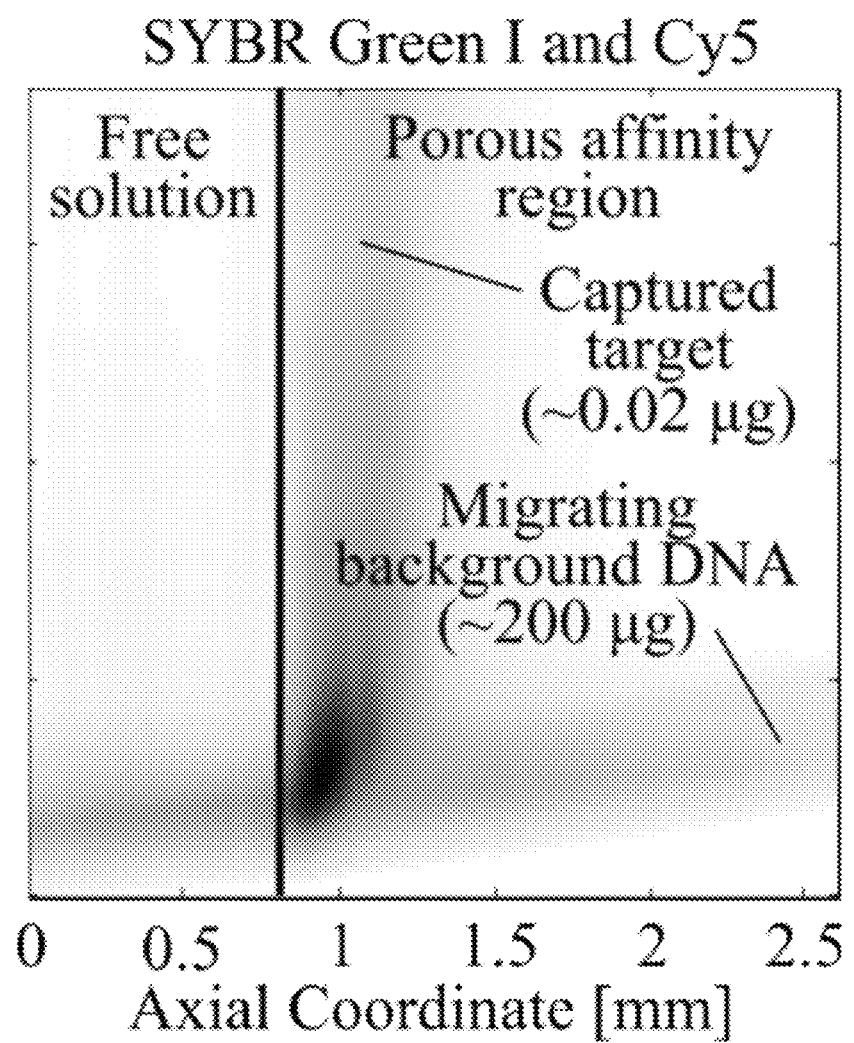

In FIG. 6C, we show the spatiotemporal plot of observed fluorescence from the experiment in both the SYBR Green I and Cy5 channels. FIG. 6C shows that while all of the target species attains zero velocity in the time scale on the order of $p_t$, the contaminant species continues to migrate at finite velocity. If the contaminant species is focused in ITP and its mobility is not changed by the affinity substrate, it will continue to migrate in ITP, at the ITP velocity. In this experiment the contaminant was fish sperm DNA and its mobility was not visibly affected by presence of PPM, hence it still migrated in ITP. This allows for superior separation as the target and contaminant are spatially confined to two distinct, sharply bounded regions. Such separations take significantly more time to achieve in traditional AC (since the target species attains zero velocity at time ~$p_t$, and $p_t$ for traditional AC is much larger then ITP-AC, see Section 2.4). Furthermore, in traditional AC if the wash step is not complete, the target zone may contain contaminant species, unlike in ITP-AC where the wash steps are already integrated (see Section 2.1). Such separations are also difficult to obtain with electrophoresis. In ITP-AC, post capture, both the target region and the contaminant region (provided it is still focused in ITP) remain the same width over time. While in addition, the separation distance between them grows proportionally with time. However, in electrophoresis, while the separation distance grows proportionally with time, the separated zones broaden overtime due to dispersion (which scales proportional to $\sqrt{t}$) (Landers, Handbook of capillary electrophoresis, CRC press, 1997; Giddings (1969) Sep. Sci. Technol. 4:181-189). Hence, the resolution in ITP-AC is higher than that in electrophoresis.

5. Conclusions

We have developed and demonstrated a method in which we combined ITP and AC to achieve faster purification and higher column utilization than possible with traditional AC. We employed ITP separation to limit the species introduced into the affinity column, excluding species that may foul the column. We leveraged ITP preconcentration to increase the target concentration and therefore accelerate the target-ligand probe reaction on the affinity substrate. Furthermore, by applying the target onto the column with ITP we obviated the need for high pressure specialized pumps and directly integrated an automatic wash step into the process, eliminating a separate wash step.

We discussed the practical aspects of coupling ITP with AC. We then developed an analytically solvable one-dimensional transport model for ITP-AC for a semi-infinite AC column and second order reversible affinity reaction. Our model captured the spatiotemporal dynamics of target-probe binding in the affinity region. Using our model and controlled experiments, we explored the coupled effects of target distribution width, distribution intensity, application velocity, forward and reverse reaction constants, and probe concentration on necessary affinity region length, assay time, and capture efficiency. Our new analytical approach allows us to collapse these six independent variables down to three non-dimensionalized parameters: $\alpha$, $\beta$, and Da. Scaled capture length (length necessary to capture 95% of the target scaled by the advection-reaction length scale) is invariant of Da for Da<1 and equals ~2.8. For Da>1, the affinity region is locally saturated and scaled capture length increases linearly with Da. Maximum capture efficiency n/N increases linearly with Da for Da<1. For Da>1, the affinity region is locally saturated and n/N=1. Scaled capture time (time necessary to capture 95% of the target scaled by the reaction time scale) increases linearly with Da/$\alpha$ for Da/$\alpha$>1. For Da/$\alpha$<1 scaled capture time, decreases with decreasing Da/$\alpha$ and asymptotes to ~4.3. This implied that for situations where Da/$\alpha$>1, target preconcentration, such as with ITP (which decreases Da/$\alpha$), can greatly reduce AC assay time and increase column utilization.

We validated our model with ITP-AC experiments with Cy5 labeled synthetic DNA target and synthetic DNA probe immobilized onto a ~2 μm pore size porous polymer monolith inside a 500 μm glass capillary. We described our choice of the porous polymer monolith affinity substrate, poly(glycidyl methacrylate-co-ethylene dimethacrylate). This substrate was non-sieving and did not exhibit non-specific binding, therefore allowed for specific separation of large macromolecules. Next, we described the synthesis of GMA-EDMA PPM and the functionalization of the PPM with DNA probes. We then described the ITP-AC protocol and choice of buffer chemistry for ITP-AC of DNA. We performed model ITP-AC experiments and compared these with our model. The predicted scaled capture length and maximum capture efficiency agreed very well with that experimentally measured for 4 orders of magnitude of Da.

Lastly, using our technique, we demonstrated sequence specific purification of 25 nucleotide target DNA and demonstrated that the resolution in ITP-AC can be higher than that in traditional AC or electrophoresis. In this experiment we successfully purified a 25 nucleotide target DNA from 10,000-fold more abundant background (contaminating) genomic fish sperm DNA in 2 mm length of column in under 500 seconds.

Example 2

Increasing Hybridization Rate and Sensitivity of DNA Microarrays Using Isotachophoresis Here we present a novel technique to accelerate and control microarray hybridization using isotachophoresis (ITP) focusing of single-stranded DNA (ssDNA) targets. We use ITP to focus and transport target molecules over arrays of probe sites. The ITP focusing dynamics strongly increase target concentration and simultaneously enhance local mixing through secondary flows and non-axial electric field components near the ITP focus zone (Garcia et al. (2013) Bull. Am. Phys. Soc. Vol. 58). ITP is an electrophoretic focusing technique, where target analyte ions are focused selectively between the leading and trailing electrolyte ions of two buffers. Relevant to the current work, ITP has been demonstrated as a means of purification and focusing of nucleic acids from complex samples (see review by Rogacs et al. (J Chromatogr A. (2014) 1335:105-120). ITP has also been demonstrated as method of dramatically speeding up reaction rates (Persat et al. (2011) Anal Chem. 83(6):2310-2316; Eid et al. (2013) Analyst 138:3117-3120; Garcia-Schwarz et al. (2012) Anal. Chem. 84:6366-6369; Garcia-Schwarz et al. (2013) Angew. Chem. Int. Ed. Engl. 52:11534-11537; Bercovici et al. (2012) Proc. Natl. Acad. Sci. U.S.A. 109:11127-11132; Bercovici et al. (2013) Analyst 138:87-90). In the latter studies, ITP was used to extract and co-focus nucleic acid targets with cDNA probes and speed up $2^{nd}$ order hybridization reactions by as much as 14,000-fold (Bercovici et al, supra). However, in all of this work, ITP was used to speed up hybridization reaction of two simultaneously focused species free in solution. In the current paper, we leverage high accumulation power of ITP to achieve both rapid and sensitive hybridization involving surface-immobilized probes. The current work also extends ITP-accelerated reactions to multiplexed detection of 20 target species. We experimentally demonstrate 30-fold (15 hours to 30 minutes) speed up of highly specific array hybridization using oligonucleotide targets and their complementary immobilized capture probes. Our system consists of a single layer PDMS channel and glass slide on which up to 60 probe spots are printed. Our technique enables quantitative detection of 26 nucleotide single stranded DNA over a dynamic range of 4 orders of magnitude, with an 8.2-fold increase in sensitivity (over conventional overnight hybridization) at 100 fM target concentration.

Overview of ITP-Enhanced DNA Array Hybridization

FIG. 7A presents schematics of our ITP enhanced microarray hybridization assay performed in three steps: initial focusing, a diffusive homogenization step, and hybridization and transport. In the focusing step, we apply high electric field to rapidly accumulate DNA targets at the moving ITP interface. The number of molecules accumulated in this step is determined by volume of the focusing channel and buffer composition (Khurana et al. (2008) Anal Chem. 80(1):279-286). During this stage, high electric field can cause electrokinetic flow instabilities which distort the ITP zone (Persat et al. (2009) New J. Phys. 11:075026). To correct this, the ITP zone is positioned within a narrow constriction where we deactivate the electric field (for about 2 minutes). This process redistributes the sample via molecular diffusion. We then re-apply electric field but now at a low constant current (2-16 µA), which avoids further instabilities and causes migration of the focused targets at constant velocity over the microarray. Microarray spots located immediately downstream of the constriction are exposed to highly focused target DNA for a finite, local residence time of the moving ITP zone (typically <300 seconds). The hybridization reaction is greatly accelerated and the progression of the ITP zone downstream then acts as an electrokinetic wash that removes unbound target. After the sequence of events depicted here, the channel containing the array is washed with wash buffers and dried out prior to scanning on the microarray scanner.

Materials and Methods

Buffers, Reagents and DNA sequences

We used twenty synthetic target-probe molecule pairs composed of perfectly complementary DNA and cDNA. We named target-probe pairs by numbers from 1 to 20. The target sequences were synthesized with Cy3 dye at the 5' terminus. Capture probes were synthesized with amine group on a C6 linker on the 5' end with additional hexa-ethylene glycol linker (HEG) separating from the DNA sequence. Additionally, we purchased and used as corner markers synthetic DNA with amino modifier C6 at the 5' terminus and Cy3 at the 3' terminus. All oligonucleotides were purchased from Integrated DNA Technologies (IDT, Coralville, Iowa), and 100 µM of their stock solutions were prepared in water and stored at −20° C.

For ITP hybridization, the aqueous LE buffer inside the channel, LE1, contained 250 mM HCl, 500 mM Tris, 5 mM $MgCl_2$, 0.1% w/w 1 MDa poly(vinylpyrrolidone) (PVP), 10% Formamide, and 0.01% w/w Tween 20. The gel-phase LE buffer in the LE reservoir, LE2 was composed of 250 mM HCl, 500 mM Tris, and 25% w/v Pluronic F-127. At 25% concentration of Pluronic F-127, the solution is a liquid below +4° C., but quickly changes to a solid-phase as it is transferred to the reservoir and exposed at room temperature (Vadnere et al. (1984) Int. J. Pharm. 22:207-218). We used this thermal gelation property to prevent pressure driven flow in the channel during ITP (Marshall et al. (2013) Proceedings of American Institute of Chemical Engineers Annual Meeting, San Francisco). The aqueous TE buffer contained 25 mM HEPES, 50 mM Bistris, 1% PVP, and varying concentrations of mixture of targets from 100 fM to 10 nM. For our comparison experiments of conventional hybridization, the hybridization buffer included target DNA diluted in the aqueous LE 1 buffer to a final concentration from 100 fM to 10 nM.

HCl, HEPES, Tris, Bis-tris, $MgCl_2$, Pluronic F-127, Tween 20 were purchased from Sigma-Aldrich (St. Louis, Mo.). PVP was obtained from Polysciences, Inc. (Warrington, Pa.). Formamide was purchased from Invitrogen (Grand Island, N.Y.). All solutions were prepared in Ultra-Pure DNase free distilled water (GIBCO Invitrogen, Carlsbad, Calif.).

Microarray

The microarrays were manufactured by Applied Microarrays, Inc. (AMI, Tempe, Ariz.) using a proprietary non-contact piezoelectric spotting equipment. Glass slides with epoxysaline coating (Schott Nexterion Slide E, Elmsford, N.Y.) were used as the substrate for immobilization. One slide had 6 identical microarrays, each consisting 8 repeated spots for 20 probe sequences (total 160 spots). The spot diameter was 60 µm, and the center-to-center distance between spots was 150 µm. The corner marker DNA was immobilized to indicate the location and the direction of the microarrays. Since the custom printing service included a blocking step after immobilization, we performed no further blocking before hybridization. Once opened from their packaging, we stored the unused microarrays in a vacuumed desiccator (Bel-Art Scienceware, Wayne, N.J.).

Fabrication of Microfluidic Device

We designed a single layer polydimethylsiloxane (PDMS) microfluidic channel consisting of 1 inlet and 1 outlet for both rapid ITP hybridization and conventional hybridization without ITP. The channel was 500 µm wide, 80 mm long and 40 µm deep, and had a 200 pm wide constriction just upstream of the probe sites. Optimized, low-dispersion turns were used to minimize dispersion of sample at turns (Molho et al. (2001) Anal. Chem. 73:1350-1360).

We used a SU-8 master mold fabricated by the Stanford Micro fluidics Foundry as a positive cast for the microfluidic channels. The PDMS precursor and curing agent (Sylgard 184, Dow Corning, Menlo Park, Calif.) were mixed thoroughly at a ratio of 20:1 (w/w), then the mixture was poured over the master mold. After degassing for 30 minutes, we cured the mixture at 65° C. for at least 6 hours. After peeling off the PDMS slab, holes were punched at the locations of reservoirs. We manually aligned the PDMS slab and glass slide based on alignment mark printed on the PDMS, and created reversible contact bond between them. We found a precursor to curing agent weight ratio of 20:1 worked very well to form a spontaneous seal between the PDMS slab and epoxysalinecoated glass slide without plasma treatment. We observed no leakage of these bonds. The final microfluidic system contained 40-60 spots within the fluidic channel, depending on the alignment.

ITP Hybridization and Conventional Hybridization

Immediately before each experiment, we primed the channel by flushing with 50% ethanol (Sigma-Aldrich, St. Louis, Mo.) for 5 minutes. This reduced the air bubble formation due to hydrophobic surface property of PDMS (Spehar et al. (2003) Electrophoresis 24:3674-3678). We completely dried the ethanol using a vacuum line for 2 minutes before filling the channel with LE1. As described in FIG. 7A, ITP hybridization requires three buffers: LE1, LE2, and TE. After filling the channel with LE1 buffer, we rinsed the two reservoirs using deionized water, and emptied thoroughly with vacuum. We pipetted 20 pL of gel-phase LE buffer (LE2) and aqueous TE buffer into the LE and TE reservoirs respectively. We then placed platinum wire electrodes into the each reservoir. The LE2 buffer changed from liquid to solid phase immediately after it was pipetted into the well from the ice bath. ITP enhanced hybridization experiments were initiated by applying 1100 V to the LE well and grounding the TE well using high voltage sourcemeter (2410, Keithley Instruments, Cleveland, Ohio). We turned off the field as the ITP zone arrived at the constriction and waited for 2 minutes. Hybridization was performed by applying constant current of 2 or 4 pA.

For conventional hybridization experiments, we followed the same priming protocol, and filled the channel with the hybridization buffer. The inlet and outlet reservoirs were then filled with 15 pl of hybridization buffer. We taped the PCR sealer (Microseal B Adhesive Sealer, MSB-1001, BIO-RAD) on top of the PDMS channel to prevent evaporation, and wrapped the entire device with aluminum foil. The microfluidic system was then incubated at room temperature for a 15 hours.

After each ITP and conventional hybridization experiment, we emptied both reservoirs, and filled the channels with 1× saline-sodium citrate (SSC, Invitrogen, Carlsbad, Calif.) for 1 minute, then completely dried the channels. We then detached the PDMS channel, and carried out further two-step washing inside a 50 ml centrifuge tube. The microarray slide was first dipped into a solution containing 0.1×SSC and 0.1% w/w TritonX (Sigma-Aldrich St. Louis, Mo.) for 1 min, and then transferred to 0.1×SSC for 1 minute. At the end of this serial wash, we dried the microarray slides completely by blowing air from compressed air can.

Detection

For the on-chip visualization of microarray hybridization shown in FIG. 7B, we used an inverted epifluorescence microscope (Eclipse TE300) (Nikon, Tokyo, Japan) equipped with a 10× objective (Plan, NA 0.45, Nikon, Tokyo, Japan). We used 100-W mercury bulb (Ushio Inc., Tokyo, Japan) and XF102-2 filter cube from Omega Optical (Brattleboro, Vt.) for excitation of Cy3 fluorophore. We recorded images with generation III, intensified CCD camera (IPentaMAX; Roper Scientific, Trenton, N.J.), controlled with Winview32 (Princeton Instruments, Trenton, N.J.). For all other results, the microarray slides were scanned at a resolution of 5 μm using a GenePix 4000B array scanner (Axon Instrument, Calif.) located in Stanford functional genomic facilities (SFGF). We used laser power of 100%, and PMT gains at 400 or 800. We used GenePix Pro 6.0 software (Axon Instrument, CA) to extract images and obtain quantitative estimate of fluorescence intensity from each spot.

Theory

We here present an analytical framework, which we use to compare ITP-enhanced surface hybridization with traditional hybridization. The model also serves to guide design and optimization of ITP hybridization experiments. In all cases, we model the surface binding reaction as a second order reaction with reaction off- and on-rate constants, $k_{off}$ and $k_{on}$, respectively, and dissociation constant $K=k_{off}/k_{on}$ (Levicky et al. (2005) Trends Biotechnol. 23:143-149). The reaction between immobilized probe (P) and suspended target (T) forming a hybrid species (H) can be expressed as follows:

$$P + T \underset{k_{off}}{\overset{k_{on}}{\rightleftharpoons}} H(i) \frac{d\tilde{C}_H}{dt} = k_{on} C_T (\tilde{C}_{H_0} - \tilde{C}_H) - k_{off} \tilde{C}_H (ii) \quad (1)$$

where $\tilde{C}_H$ and $\tilde{C}_{H0}$ respectively denote molar surface concentration of hybrid pairs and of free binding sites at t=0 in units of mol/m². $C_T$ is volumetric target concentration with units of mol/m³.

In conventional microarray hybridization, order 15 hour incubation is used to drive surface reactions to near completion. At equilibrium, the fraction of hybridized probes, $h_{conven}$, defined as the ratio of $\tilde{C}_H$ and $\tilde{C}_{H0}$, can be expressed as $$h_{conven} = \frac{C_0^*}{C_0^* + 1}, \quad (2)$$

where $C_0^*$ denotes the initial target concentration, $C_0$, normalized by K. Equation (2) assumes the initial concentration of target remains unchanged at the equilibrium. This approximation is valid for most microarray analyses (Pappaert et al. (2006) Biotechnol. 123:381-396). Note that fraction of the hybridized probe is directly proportional to the initial target concentration in the regime of $C_0^* \ll 1$, which is the desired design criterion for quantitative microarray analysis. Further, initial target concentration limits the theoretical maximum signal of the assay. This limitation has prompted the use of long incubation times, in efforts to approach thermodynamic equilibrium and maximize sensitivity (Bhanot et al. (2003) Biophys. J. 84:124-135; Sartor et al. (2004) Biotechniques 36:790-796). Similarly, vigorous mixing is used to remove any diffusion limitation and approach equilibrium via reaction regimes limited solely by $k_{on}$.

As we shall see below, ITP enables disruption of this typical paradigm by strongly increasing local target concentrations. Increased target concentration both improves the rate of capture and increases the local maximum signal attainable at this high concentration. ITP is also known to cause secondary flows33 and this helps avoid diffusion-limited regimes. Heterogeneous (i.e., molecule in solution to surface-bound ligand) DNA hybridization generally progresses through two phases before it reaches equilibrium: kinetically limited regime for small times, and transition to a diffusion limited regime (Pappaert et al. (2003) Chem. Eng. Sci. 58:4921-4930; Pappaert et al. (2006) Biotechnol. 123:381-396). Because of its strong preconcentration, ITP results in a signal above that of equilibrium within a time scale limited by the residence time of the focus zone over each reaction site (c.f. FIG. 7B). We therefore model ITP hybridization assay as a kinetically limited reaction. We verify the validity of this assumption using typical parameter values for our system and Pappaert et al. (Biotechnol. (2006) 123:381-396) nondimensional analysis on heterogeneous DNA hybridization. The details of the latter calculation can be found in ESI.

Assuming kinetically limited ITP hybridization, we can approximate the dynamics of fraction of surface probes hybridized as follows (Vijayendran et al. (1999) Anal. Chem. 71:5405-5412; Phillips et al. (2010) J. Chromatogr. B 878:228-236; Hagan et al. (2004) J. Chem. Phys. 120:4958-4968):

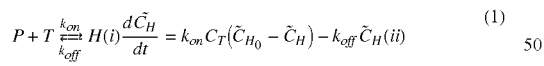

$$h_{kin} = \frac{C_0^*}{C_0^* + 1} (1 - \exp(-(C_0^* + 1)k_{off} t)). \quad (3)$$

This expression was derived by Vijayendran et al. (Anal. Chem. (1999) 71:5405-5412) for kinetic limited hybridization reaction, and applies to either small time limit or well-mixed cases (or both). As a simple approximation, we approximate the concentration profile of ITP focused target as a tophat pulse with peak concentration value of $pC_0$ and width of $\delta_{ITP}$, traveling at a known, constant velocity of $V_{ITP}$. Here p denotes the fold preconcentration level of the target species in the ITP zone compared to the initial concentration. Under this simple model of an ITP zone, we estimate the time that immobilized probe is exposed to the high concentration target as the residence time, $t_{res}=\delta_{ITP}/V_{ITP}$. Therefore, we model that ITP hybridization is performed for a short, finite time of $t_{res}$ at concentration of $pC_0$. We substitute the appropriate concentration and time terms in the kinetically limited solution above with those of ITP hybridization, and express the fraction of hybridized probes as $$h_{ITP} = \frac{pC_0^*}{pC_0^* + 1}(1 - \exp(-(pC_0^* + 1)k_{off}t_{res})). \quad (4)$$

This simple model yields insight into ITP-aided hybridization dynamics and will serve as a comparison case for the conventional hybridization run at equilibrium.

Equation (4) shows that the preconcentrated target associated with ITP-aided hybridization helps in three ways: it achieves fast reaction, improves sensitivity, and can enable quantitative detection. First, ITP preconcentration greatly accelerates the reaction by enabling high initial reaction rate that scales asp, which can be seen by taking derivative of Equation (4) with respect to $t_{res}$. As usual with acceleration techniques in microarray, we compare the time to obtain the same signal intensity for both methods. For conventional diffusion-limited hybridization, we assume equilibrium is reached after 15 hours based on common microarray protocols. We then calculate ITP residence time needed to reach the fraction of hybridized probe at the equilibrium of conventional hybridization, $\hat{t}_{res}$. By equating Equation (2) and (4), and rearranging in terms of residence time term, we obtain the expression of $\hat{t}_{res}$ as $$\hat{t}_{res} = \frac{\ln\left(\frac{pC_0^* + p}{p - 1}\right)}{k_{off}(pC_0^* + 1)}. \quad (5)$$

Using typical parameters of our system given as $C_0^*=0.01$, $p=500$, and $k_{off}=10^{-4}$ s$^{-1}$, we calculate $\hat{t}_{res}$ to be 20 seconds. Comparing this example case with 15 hour hybridization time of conventional method, the speed-up constitutes 2700 fold for one column of spots in the span-wise direction of microchannel (2-3 spots in our system). For multiple columns, the total ITP hybridization time should be calculated as $\hat{t}_{res}$ multiplied by the ratio of total length of the array to ITP width.

Second, we see an increase of sensitivity for ITP enhanced hybridization. In FIG. 8, we present contours representing the ratio of fraction hybridized of ITP hybridization and conventional hybridization versus nondimensional time, $k_{off}t_{res}$, and preconcentration level, p. We observe that the ratio higher than 1 is achieved for the range of parameters indicated by gray area. The square symbol represents the condition used for the experimental data shown in the FIG. 9. The theory predicts increase in sensitivity by 5.6 fold, and we experimentally observed 8.2-fold increase in signal. As shown with the example case, ITP's high accumulation power can easily achieve sensitivity improvement over conventional hybridization method. We note that the abscissa and ordinate are not completely independent because p and $t_{res}$ are both function of electric field. However we choose this representation because the dimensionless parameters on the axes facilitate the comparison with experimental conditions.

Third, ITP hybridization enables quantitative detection for a wide dynamic range, fulfilling the prime criterion as an analytical technique. For the case of $(pC_0^*+1)k_{off}t_{res}\ll 1$, a Taylor series expansion of the exponential function reveals a direct proportionality between fraction hybridized and the initial concentration: $h_{ITP}\approx pk_{on}t_{res}C_0$. Also, the proportionality factor for ITP includes the ITP parameters p and $t_{res}$, which gives designers flexibility to determine the concentration range yielding the linear proportionality. One key difference compared from the conventional hybridization is that ITP hybridization achieves the linear proportionality not by pushing the reaction to the equilibrium, but by freezing the reaction before it enters the diffusion limited regime. Again, this is possible because strong preconcentration greatly accelerates initial reaction rate, and increases signal in a short time.

Results and Discussion

Demonstration of Microarray Hybridization Acceleration

We first performed on-chip visualization experiments of ITP hybridization process using standard epifluorescence microscopy with CCD camera imaging. In FIG. 7B, we present images taken from a single ITP microarray hybridization experiment at three times. Here, we focused twenty Cy3 labeled ssDNA target sequences at 100 pM initial concentration, and let the ITP zone pass over spots with immobilized probes. Initially, the probes were in contact with LE solution containing no target species, thus we observed no fluorescence signal. After the ITP zone passes over the reaction spots, we observed fluorescence intensity increase, as expected. The background signal in these images is higher in the trailing zone of ITP peak as the TE contains target species. These images serve as a qualitative description of the assay.

Quantitative and High Sensitive Detection

We demonstrate wide quantitative detection dynamic range, high sensitivity, and hybridization acceleration of our technique by comparing titration curves for ITP and conventional hybridization. In FIG. 9, we present experimental data of fraction of hybridized probes against six concentrations for ITP (triangle) and conventional hybridization (circle). The hybridization experiments were performed using a mixture of twenty target sequences at initial concentrations varying from 100 fM to 10 nM. Here we show results from only target 1, but we include more data for additional targets in ESI.

The fraction of hybridized probe was estimated from experiments by normalizing the background-subtracted fluorescence signal with the maximum value for the respective methods. In both cases, we observed that the fraction of hybridized probe proportionally increased with increasing concentration over a dynamic range of 4 orders of magnitude. The fraction hybridized for ITP hybridization was higher than that of conventional hybridization for all concentrations, showing improved sensitivity due to the preconcentration effect of ITP. For example, in the inset, we compare the raw fluorescence intensities for ITP and conventional hybridization (here, without background subtraction) for the lowest concentration case (100 fM) and a negative control of no target in solution. Intensity increase relative to the negative control was 1.7 for conventional and 14 for ITP hybridization; this implies an 8.2 fold increase in sensitivity for ITP hybridization. The ITP assay total duration (for all spots) was 30 minutes, compared to 15 hours for the conventional hybridization; a 30-fold speed up for the process.

Shown together with the experimental data set are analytical models for the conventional and ITP hybridization (dashed and solid lines). To obtain these theoretical curves, we first fit the conventional hybridization data with the equilibrium model of Eq. (2) using K as a single fitting parameter. The fitting parameter was determined as K=5.7× 10$^{-10}$ M using 'nlinfit' function of Matlab. For the ITP model, we used the same value of K and together with independently measured estimate values of p=549 and $t_{res}$=235 seconds. The single fitting parameter for the ITP hybridization prediction was determined as $k_{on}$=7.6×10$^5$ M$^{-1}$ s$^{-1}$. These kinetic parameter values are typical for heterogeneous hybridization (Okahata et al. (1998) Anal. Chem. 70:1288-1296; (Henry (1999) Anal. Biochem. 276: 204-214; Tawa et al. (2004) Nucleic Acids Res. 32:2372-2377). For ITP, we observed good qualitative agreement of predicted trends and our experimental data. For conventional hybridization, we observed good qualitative agreement at higher concentrations, but a slight discrepancy at lower concentrations. We hypothesize that the conventional hybridization may not have reached the equilibrium in 15 hours for the lowest target concentrations explored. experimental data (symbols), we show results of analytical models with a respective fitting parameter for ITP (solid) and conventional (dashed) hybridization. Inset compares fluorescence intensity from $C_0$=100 fM hybridization data of both methods and the negative control with no target. The fluorescence intensity from each method divided by the negative control was 1.7 for conventional and 14 for ITP hybridization, corresponding to 8.2-fold increase in sensitivity for 30 minute ITP hybridization. The range bar was used to indicate maximum and minimum data points (N=3).

Comparison of Non-Specific Signal for ITP and Conventional Hybridization

In FIG. 10, we present measurements of specific and non-specific signal obtained with conventional and ITP hybridization. For this demonstration, we included only one target (target 1) at an initial concentration of 100 pM, and performed conventional and ITP-aided hybridizations. After hybridization, we recorded the raw fluorescence intensity from all 20 probe sequences. The bar plots represent the background-subtracted fluorescence intensity resulting from specific (for target 1, white) and nonspecific (for target numbers 2-20, gray) hybridization. The specific signal of ITP was higher than the conventional case. The nonspecific signals for both conventional and ITP hybridization were of the same order of magnitude. For most of the sequences, the non-specific signal was lower than the local background signal, indicating low level non-specific binding of DNA or dye to the array surface. To obtain a quantitative measure for specificity, we calculated a specificity index defined as the ratio of specific signal to the highest nonspecific signal (target 4). The specificity index was 160 for conventional hybridization and 2130 for ITP hybridization.

CONCLUSION

We demonstrated the acceleration and sensitivity improvement of DNA microarray hybridization using ITP. Our method leverages high preconcentration power of ITP to overcome the slow reaction kinetics of surface hybridization. We focus target molecules in a narrow (order 100 μm) ITP zone, transport them over immobilized probes, and speed-up the surface binding reaction. Our approach enabled 30 fold shorter hybridization assay time compared to the overnight conventional hybridization, and at the same time improved the sensitivity by nearly one order of magnitude without increasing nonspecific signal. The current paper is also the first ITP-based hybridization work demonstrating the quantitative analysis for over 10-plex multiplexed detection (total 60 spots, 20 sequences). We believe that our technique can be easily adapted for high density DNA array by upscaling the dimension of the device. Furthermore, the current study can be merged with ITP's nucleic acid extraction functionality to make an integrated on-chip nucleic acid analysis system that inputs complex sample and outputs the quantitation of several sequences. Since ITP preconcentration is applicable to a wide range of biological molecules, we hypothesize that the method presented here is generally applicable to accelerate other ligand-analyte binding processes such as antigen-antibody, hapten-antibody or protein-aptamer. Rapid and sensitive ITP microarray hybridization holds the potential to speed-up traditionally long assays for applications in clinical diagnostics.

While the preferred embodiments of the invention have been illustrated and described, it will be appreciated that various changes can be made therein without departing from the spirit and scope of the invention.

What is claimed is:

1. A method of increasing a rate and a degree of completion of a reaction between a first reactant in a liquid phase and a second reactant on a surface of a solid, the method comprising:
   a) contacting the solid with the liquid phase;
   b) concentrating the first reactant in the liquid phase near the second reactant on the surface of the solid by performing isotachophoresis (ITP) within the liquid phase using a trailing electrolyte (TE) and a leading electrolyte (LE), such that the first reactant in the liquid phase is concentrated at a LE-TE interface near the second reactant on the surface of the solid;
   c) reacting the first reactant in the liquid phase with the second reactant on the surface of the solid; and
   d) removing the liquid phase by displacing the liquid phase with an immiscible liquid or a gas, thereby impeding the reverse reaction and increasing the rate and the degree of completion of the reaction.

2. The method of claim 1, wherein the reaction comprises binding of the first reactant to the second reactant.

3. The method of claim 2, wherein the first reactant is a target molecule and the second reactant is an affinity ligand immobilized on the solid.

4. A device for performing ITP in combination with affinity chromatography according to the method of claim 3, the device comprising:
   a) a tube comprising an input end and an output end;
   b) an affinity region comprising a plurality of affinity ligands immobilized on a solid support, wherein the affinity region is located inside the tube;
   c) a first reservoir comprising the TE, wherein the first reservoir is connected to the input end of the tube; and
   d) a second reservoir comprising the LE, wherein the second reservoir is connected to the output end of the tube.

5. The device of claim 4, wherein the solid support comprises a porous polymer monolith (PPM).

6. The device of claim 5, wherein the PPM comprises an acrylate, methacrylate, vinylpyridine, vinylpyrrolidone, vinylbenzene, divinylbenzene, or vinyl acetate polymer.

7. The device of claim 6, wherein the PPM comprises poly(glycidyl methacrylate-co-ethylene dimethacrylate) (GMA-EDMA).

8. The device of claim 5, wherein the PPM has pores of at least 1 micron in diameter.

9. The device of claim 4, wherein the tube is a capillary, chromatography column, or a microfluidic channel.

10. The device of claim 4, wherein the affinity region has a hydrodynamic resistance low enough to allow the tube to be filled without the use of a high pressure pump.

11. A method for performing affinity chromatography with the device of claim 4, the method comprising:

a) filling the second reservoir and the tube with a solution comprising the LE;
b) adding a solution comprising the target molecule and the TE to the first reservoir;
c) performing isotachophoresis (ITP), such that the target molecule is concentrated at a LE-TE interface in the affinity region;
d) capturing the target molecule by binding the target molecule to an affinity ligand in the affinity region;
e) removing the solution comprising the LE and the solution comprising the TE by adding an immiscible liquid or gas to the tube; and
f) eluting the target molecule.

12. The method of claim 2, wherein the first reactant is a target nucleic acid and the second reactant is a nucleic acid probe immobilized on the solid.

\* \* \* \* \*